(12) United States Patent
Colvin, Jr. et al.

(10) Patent No.: US 10,905,355 B2
(45) Date of Patent: Feb. 2, 2021

(54) ELECTRODYNAMIC FIELD STRENGTH TRIGGERING SYSTEM

(71) Applicant: Senseonics, Incorporated, Germantown, MD (US)

(72) Inventors: Arthur E. Colvin, Jr., Mt. Airy, MD (US); Andrew DeHennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

(21) Appl. No.: 16/573,438

(22) Filed: Sep. 17, 2019

(65) Prior Publication Data

US 2020/0015705 A1 Jan. 16, 2020

Related U.S. Application Data

(63) Continuation of application No. 16/049,334, filed on Jul. 30, 2018, now abandoned, which is a
(Continued)

(51) Int. Cl.
*A61B 5/07* (2006.01)
*A61B 5/00* (2006.01)
*A61B 5/145* (2006.01)

(52) U.S. Cl.
CPC ............ *A61B 5/076* (2013.01); *A61B 5/0031* (2013.01); *A61B 5/14503* (2013.01); *A61B 5/0022* (2013.01); *A61B 2562/0257* (2013.01)

(58) Field of Classification Search
CPC ... A61B 5/076; A61B 5/0031; A61B 5/14503; A61B 5/0022; A61B 2562/0257
See application file for complete search history.

(56) References Cited

U.S. PATENT DOCUMENTS

| 4,251,808 A | 2/1981 | Lichtbiau |
| 4,679,046 A | 7/1987 | Curtis et al. |

(Continued)

FOREIGN PATENT DOCUMENTS

| JP | H2-31738 A | 2/1990 |
| JP | 2004-502252 A | 1/2004 |

(Continued)

OTHER PUBLICATIONS

Catrysse, M., et al., "An inductive power system with integrated bi-directional data-transmission," Sensors and Actuators A, vol. 115, No. 2-3, pp. 221-229, XP004562075, ISSN: 0924-4247 (Sep. 21, 2004).

*Primary Examiner* — Brian A Zimmerman
*Assistant Examiner* — Kevin Lau
(74) *Attorney, Agent, or Firm* — Rothwell, Figg, Ernst & Manbeck, P.C.

(57) ABSTRACT

Systems and methods for automatically triggering wireless power and data exchange between an external reader and an implanted sensor. The implanted sensor may measure the strength of an electrodynamic field received wirelessly from the reader and convey field strength data based on the measured strength of the received electrodynamic field to the reader. If the field strength data indicates that the strength of an electrodynamic field received by the sensor is sufficient for the implanted sensor to perform an analyte measurement, the reader may convey an analyte measurement command to the sensor, which may execute the analyte measurement command and convey measurement information back to the reader. The systems and methods may trigger the analyte measurement as the reader transiently passes within sufficient range/proximity to the implant (or vice versa).

6 Claims, 24 Drawing Sheets

Related U.S. Application Data continuation of application No. 15/430,198, filed on Feb. 10, 2017, now Pat. No. 10,034,619, which is a continuation of application No. 13/650,016, filed on Oct. 11, 2012, now abandoned.

(60) Provisional application No. 61/597,496, filed on Feb. 10, 2012, provisional application No. 61/545,874, filed on Oct. 11, 2011.

(56) References Cited

U.S. PATENT DOCUMENTS

| | | | |
|---|---|---|---|
| 5,735,887 A | 4/1998 | Barreras, Sr. et al. | |
| 5,767,792 A | 6/1998 | Urbas et al. | |
| 6,118,378 A | 9/2000 | Balch et al. | |
| 6,400,974 B1 | 6/2002 | Lesho | |
| 6,731,976 B2 | 5/2004 | Penn et al. | |
| 7,782,192 B2 | 8/2010 | Jeckelmann et al. | |
| 8,940,544 B2 | 1/2015 | Suri et al. | |
| 9,184,875 B2 | 11/2015 | Sicurello et al. | |
| 9,831,985 B2 | 11/2017 | Sicurello et al. | |
| 9,907,470 B2 | 3/2018 | Goodnow et al. | |
| 9,973,238 B2 | 5/2018 | Pletcher et al. | |
| 10,069,350 B2 | 9/2018 | Stevens et al. | |
| 10,080,902 B2 | 9/2018 | Dinsmoor et al. | |
| 10,178,954 B2 | 1/2019 | Fennell et al. | |
| 2002/0072779 A1 | 6/2002 | Loeb | |
| 2003/0176785 A1* | 9/2003 | Buckman | A61B 5/1112 600/431 |
| 2004/0054385 A1 | 3/2004 | Lesho | |
| 2005/0162332 A1 | 7/2005 | Schantz | |
| 2007/0163880 A1 | 7/2007 | Woo et al. | |
| 2007/0181425 A1 | 8/2007 | Kim | |
| 2008/0129457 A1* | 6/2008 | Ritter | G07C 9/257 340/10.1 |
| 2008/0218759 A1 | 9/2008 | Colvin | |
| 2009/0171178 A1 | 7/2009 | He et al. | |
| 2009/0246080 A1* | 10/2009 | Rivet | A61B 5/14546 422/400 |
| 2009/0325593 A1* | 12/2009 | Do | H04M 1/72572 455/456.1 |
| 2010/0072994 A1 | 3/2010 | Lee et al. | |
| 2010/0145317 A1 | 6/2010 | Laster et al. | |
| 2010/0308974 A1 | 12/2010 | Rowland et al. | |
| 2011/0004076 A1 | 1/2011 | Janna et al. | |
| 2011/0213225 A1 | 9/2011 | Bernstein et al. | |
| 2011/0287808 A1 | 11/2011 | Huang | |
| 2012/0139730 A1 | 6/2012 | Kearney | |
| 2013/0265139 A1 | 10/2013 | Nummila et al. | |

FOREIGN PATENT DOCUMENTS

| | | |
|---|---|---|
| JP | 2004-513681 A | 5/2004 |
| JP | 2008-538948 A | 11/2008 |
| JP | 2010-524554 A | 7/2010 |

\* cited by examiner

ELECTRODYNAMIC FIELD STRENGTH TRIGGERING SYSTEM

CROSS-REFERENCE TO RELATED APPLICATIONS

This application is a continuation of U.S. patent application Ser. No. 16/049,334, filed on Jul. 30, 2018, which is a continuation of U.S. patent application Ser. No. 15/430,198, filed on Feb. 10, 2017, now U.S. Pat. No. 10,034,619, which is a continuation of U.S. patent application Ser. No. 13/650,016, filed on Oct. 11, 2012, which claims priority to U.S. Provisional Application No. 61/545,874, filed on Oct. 11, 2011, and U.S. Provisional Application No. 61/597,496, filed on Feb. 10, 2012, all of which are incorporated by reference herein in their entireties.

BACKGROUND

Field of the Invention

The present invention relates to a system for obtaining analyte measurements. Specifically, the present invention relates to an external reader that can interrogate an implanted analyte sensor.

Description of the Background

In a system in which an external sensor reader provides power to an implanted sensor for operation (e.g., analyte measurement) and data transfer, the primary coil of the external sensor reader must be appropriately aligned with the secondary coil of the implanted sensor. However, there is a finite and relatively short range (typically less than one inch) within which the implanted sensor receives an electrodynamic field from the external sensor reader of sufficient strength to power the sensor for analyte measurement and data transfer. In addition, finding the correct alignment is made more difficult because an implanted sensor is not visible to the user.

An attached system that physically maintains the external sensor reader in alignment with the implanted sensor using, for example, a fixed wristwatch, armband, or adhesive patch does not work well for users who do not wish to wear a wristwatch, armband, adhesive patch, or other fixed system and/or only require intermittent readings from the implanted sensor during any period in time. Furthermore, even a system that enabled on-demand measurement would be unsatisfactory if it required a user to probe around either by trial and error or by watching a field strength meter to find the relative position in space from which to initiate a reading.

RFID systems and readers are used for animal identification, anti-theft applications, inventory control, highway toll road tracking, credit card, and ID cards, but are not applicable in the context of an implantable sensor and external reader system. RFID systems are transponders, and the energy supplied must only reflect a preset numerical sequence as an ID. This requires much less power than an activated remote/implanted sensor, and an RFID system is therefore capable of much more range because of the extremely low operational power requirement from the RFID tag and can allow operation at ranges of up to 5 feet or more. In contrast, an implanted analyte sensor must be provided with much more power to operate its circuitry for making measurements and conveying the data to the reader. In fact, transfer of power by induction between two coils is very inefficient at distance, and such systems are often limited to approximately one inch or less, instead of multiple feet possible in RFID systems.

A hobby or utility grade metal detector or stud finder is also inapplicable in the context of an implanted sensor and external reader system. Metal detection or stud finding is an example of motion type operation, but the relationship between the primary coil and the metal to be detected is completely passive. Thus, in stark contrast with an implanted sensor and external reader system, where the implanted sensor requires power for activation, measurement, and data transfer, no power is required to activate the metal being detected by a metal detector or stud finder, and only the relative motion perturbation of the electromagnetic field is required.

Accordingly, there is a need for an improved implanted sensor and external reader system.

SUMMARY

One aspect of the invention is a triggering mechanism that triggers/initiates an analyte reading/measurement from an implantable sensor (e.g., an implantable chemical or biochemical sensor) as an external reader transiently passes within sufficient range/proximity to the implant (or vice versa). The movement may be relative movement (a) between a stationary implant and a transient reader, (b) between a stationary reader and a transient implant site (e.g., relative movement of a wrist implant site into and/or out of a stationary coil), or (c) relative movement between both. In some embodiments, the triggering mechanism automatically triggers the system to take a reading from the sensor at just the moment when relative movement of a handheld reader and the sensor has placed the reader within sufficient field strength range of the sensor without the user needing to probe around either by trial and error or by watching a field strength meter to find the relative position in space from which to initiate a reading. In one embodiment, the invention may automate the analyte measurement sequence and reduce the action required by the user to nothing more than movement of a handheld sensor reader.

One aspect of the invention includes a circuitry component that takes measurements of a current proportional to the field strength received by the sensor, and that indicates the relative field strength (current) or magnetic coupling between the primary coil of the reader and the secondary coil within the sensor. In some embodiments, the system detects when the sensor is within range to allow the power and data transfer and immediately sends a command within the reader to initiate the power transfer and data receiving sequence. In some embodiments, because the reading/measurement happens very fast between a sensor and reader (e.g., on the order of 10 milliseconds), the relative movement may be dynamic as relative swipe-type hand movements.

One aspect of the present invention allows either retro add-on type adaptation of reader capable platforms (e.g., smart phones) or integrated inclusion in new design of smart phones, handhelds, dedicated sensor readers, or other compatible electronic devices. In some embodiments, the present invention may enable intermittent readings to be taken automatically from an implantable sensor under the relative motion of the external sensor reader and sensor/implant site into close-enough proximity.

One embodiment of the invention is implemented by (i) taking a measure within a circuitry that contains a value (e.g., current) proportional to field strength; (ii) when that value reaches a threshold value of field strength coupling between the two coils of a reader-sensor pair, indicating that reliable power and data transfer can occur; and (iii) triggering the regular read command sequence, which then initiates the reading to be taken by the reader for subsequent display to the user. The reader may then be returned to pocket, or purse, or wherever the user keeps it until a next reading is desired.

In one aspect, the present invention provides a method of triggering a sensor implanted within a living animal to measure a concentration of an analyte in a medium within the living animal. The method may include coupling an inductive element of an external reader and an inductive element of the sensor within an electrodynamic field. The method may include generating field strength data indicative of the strength of the coupling of the inductive element of the external reader and the inductive element of the sensor. The method may include determining, based on the field strength data, whether the strength of the coupling of the inductive element of the external reader and the inductive element of the sensor is sufficient for the sensor to perform an analyte concentration measurement and convey the results thereof to the external reader. The method may include, if the strength of the coupling of the inductive element of the external reader and the inductive element of the sensor is determined to be sufficient, triggering an analyte concentration measurement by the sensor and conveyance the results thereof to the external reader.

In some embodiments, the external reader may generate the field strength data by producing, using circuitry of the external reader, a coupling value proportional to the strength of the coupling of the inductive element of the external reader and the inductive element of the sensor.

In some embodiments, the method may include producing, using circuitry of the sensor, a coupling value proportional to the strength of the coupling of the inductive element of the external reader and the inductive element of the sensor. The method may include modulating, using circuitry of the sensor, the electrodynamic field based on the coupling value proportional to the strength of the coupling of the inductive element of the external reader and the inductive element of the sensor. The external reader may generate the field strength data by decoding, using circuitry of the external reader, the modulation of the electrodynamic field. The method may include converting, using circuitry of the sensor, the coupling value into a digital coupling value. The method may include, modulating, using circuitry of the sensor, the electrodynamic field based on the digital coupling value. The external reader may generate the field strength data by decoding, using circuitry of the external reader, the modulation of the electrodynamic field.

In some embodiments, the field strength data may be a value proportional to the strength of the coupling of the inductive element of the external reader and the inductive element of the sensor. Determining whether the strength of the coupling is sufficient may include comparing the field strength data to a field strength sufficiency threshold. The strength of the coupling may be determined to be sufficient if the field strength data exceeds a field strength sufficiency threshold.

In some embodiments, the coupling may include moving the sensor and the external reader relative to each other such that the inductive element of the external reader and the inductive element of the sensor are coupled within the electrodynamic field.

In another aspect, the present invention provides a method of triggering a sensor implanted within a living animal to measure a concentration of an analyte in a medium within the living animal. The method may include generating, using an external reader, field strength data indicative of the strength of coupling of an inductive element of the external reader and an inductive element of the sensor within an electrodynamic field. The method may include determining, using the external reader, based on the field strength data, whether the strength of the coupling of the inductive element of the external reader and the inductive element of the sensor is sufficient for the sensor to perform an analyte concentration measurement and convey the results thereof to the external reader. The method may include, if the strength of the coupling of the inductive element of the external reader and the inductive element of the sensor is determined to be insufficient, repeating the generating and determining steps. The method may include, if the strength of the coupling of the inductive element of the external reader and the inductive element of the sensor is determined to be sufficient, triggering, using the external reader, an analyte concentration measurement by the sensor and conveyance the results thereof to the external reader, wherein the triggering comprises conveying, using circuitry of the external reader, an analyte measurement command to the sensor. The method may include decoding, using circuitry of the external reader, analyte measurement information conveyed from the sensor.

In yet another aspect, the present invention provides a method of triggering a sensor implanted within a living animal to measure a concentration of an analyte in a medium within the living animal. The method may include producing, using circuitry of the sensor, a coupling value proportional to the strength of the coupling of the inductive element of an external reader and an inductive element of the sensor within an electrodynamic field. The method may include converting, using circuitry of the sensor, the coupling value into a digital coupling value. The method may include conveying, using circuitry of the sensor, the digital coupling value to the external reader. The method may include decoding, using the circuitry of the sensor, an analyte measurement command conveyed from the external reader. The method may include executing, using the sensor, the analyte measurement command. The execution of the analyte measurement command may include generating, using the sensor, analyte measurement information indicative of the concentration of the analyte in the medium within the living animal. The execution of the analyte measurement command may include conveying, using the inductive element of the implanted sensor, the analyte measurement information.

In still another aspect, the present invention provides a sensor for implantation within a living animal and measurement of a concentration of an analyte in a medium within the living animal. The sensor may include an inductive element configured to couple with an inductive element of an external reader within an electrodynamic field. The sensor may include an input/output circuit configured to produce a coupling value proportional to the strength of the coupling of the inductive element of the external reader and the inductive element of the sensor within the electrodynamic field. The input/output circuit may be configured to convey a digital coupling value to the external reader. The input/output circuit may be configured to decode an analyte measurement command conveyed from the external reader. The input/output circuit may be configured to convey analyte measurement information indicative of the concentration of the analyte in the medium within the living animal. The sensor may include circuitry to convert the coupling value into a digital coupling value. The sensor may include a measurement controller configured to: (i) control the input/output circuit to convey the digital coupling value; (ii) in accordance with the analyte measurement command, generate the analyte measurement information indicative of the concentration of the analyte in the medium within the living animal; and (iii) control the input/output circuit to convey the analyte measurement information.

In another aspect, the present invention provides an external reader for triggering a sensor implanted within a living animal to measure a concentration of an analyte in a medium within the living animal. The external reader may include an inductive element configured to couple with an inductive element of an external reader within electrodynamic field. The external reader may include circuitry configured to: (i) generate field strength data indicative of the strength of coupling of an inductive element of the external reader and an inductive element of the sensor within an electrodynamic field; (ii) determine based on the field strength data, whether the strength of the coupling of the inductive element of the external reader and the inductive element of the sensor is sufficient for the sensor to perform an analyte concentration measurement and convey the results thereof to the external reader; (iii) if the strength of the coupling of the inductive element of the external reader and the inductive element of the sensor is determined to be insufficient, repeat the generating and determining steps; (iv) if the strength of the coupling of the inductive element of the external reader and the inductive element of the sensor is determined to be sufficient, trigger an analyte concentration measurement by the sensor and conveyance the results thereof to the external reader, wherein the triggering comprises conveying an analyte measurement command to the sensor; and (v) decode analyte measurement information conveyed from the sensor.

In another aspect, the present invention provides a method of triggering a sensor implanted within a living animal to measure a concentration of an analyte in a medium within the living animal. The method may include producing, using circuitry of the sensor, a coupling value proportional to the strength of the coupling of the inductive element of an external reader and an inductive element of the sensor within an electrodynamic field. The method may include determining, using the sensor, based on the coupling value, whether the strength of the coupling of the inductive element of the external reader and the inductive element of the sensor is sufficient for the sensor to perform an analyte concentration measurement and convey the results thereof to the external reader. The method may include, if the strength of the coupling of the inductive element of the external reader and the inductive element of the sensor is determined to be sufficient, executing, using the sensor, the analyte measurement command. The execution of the analyte measurement command may include: generating, using the sensor, analyte measurement information indicative of the concentration of the analyte in the medium within the living animal; and conveying, using the inductive element of the implanted sensor, the analyte measurement information.

In another aspect, the present invention provides an external reader for obtaining an analyte measurement from an implanted sensor. The reader may include a housing, reader components, and a communication member. The reader components may be configured to wirelessly communicate with the implanted sensor and obtain an analyte measurement from the implanted sensor. The reader components may comprise a coil configured to inductively couple with the implanted sensor. The communication member may be configured to communicate the analyte measurement to an electronic device.

In another aspect, the present invention provides an external reader for obtaining analyte measurements from an implanted sensor and configured to encase a smartphone including a communication port. The reader may include a first casing including a first coupling member, a second casing including a second coupling member configured to couple with the first coupling member, a communication member configured to couple with the communication port of the smartphone, and reader components. The reader components may be configured to wirelessly communicate with the implanted sensor and obtain an analyte measurement from the implanted sensor. The reader components comprise a coil configured to inductively couple with the implanted sensor.

BRIEF DESCRIPTION OF THE DRAWINGS

FIGS. 4-7 illustrate an external sensor reader that includes a smartphone and a smartphone case in accordance with an embodiment of the present invention. FIG. 4 illustrates a perspective view of an exploded sensor reader in accordance with an embodiment of the present invention.

FIG. 6 illustrates a perspective view of the smartphone case of the sensor reader without the smartphone in accordance with an embodiment of the present invention.

FIG. 7 illustrates a perspective view of the sensor reader with the smartphone case encasing the smartphone and the bottom casing shown as transparent in accordance with an embodiment of the present invention.

DETAILED DESCRIPTION OF THE PREFERRED EMBODIMENTS

Figure 1:
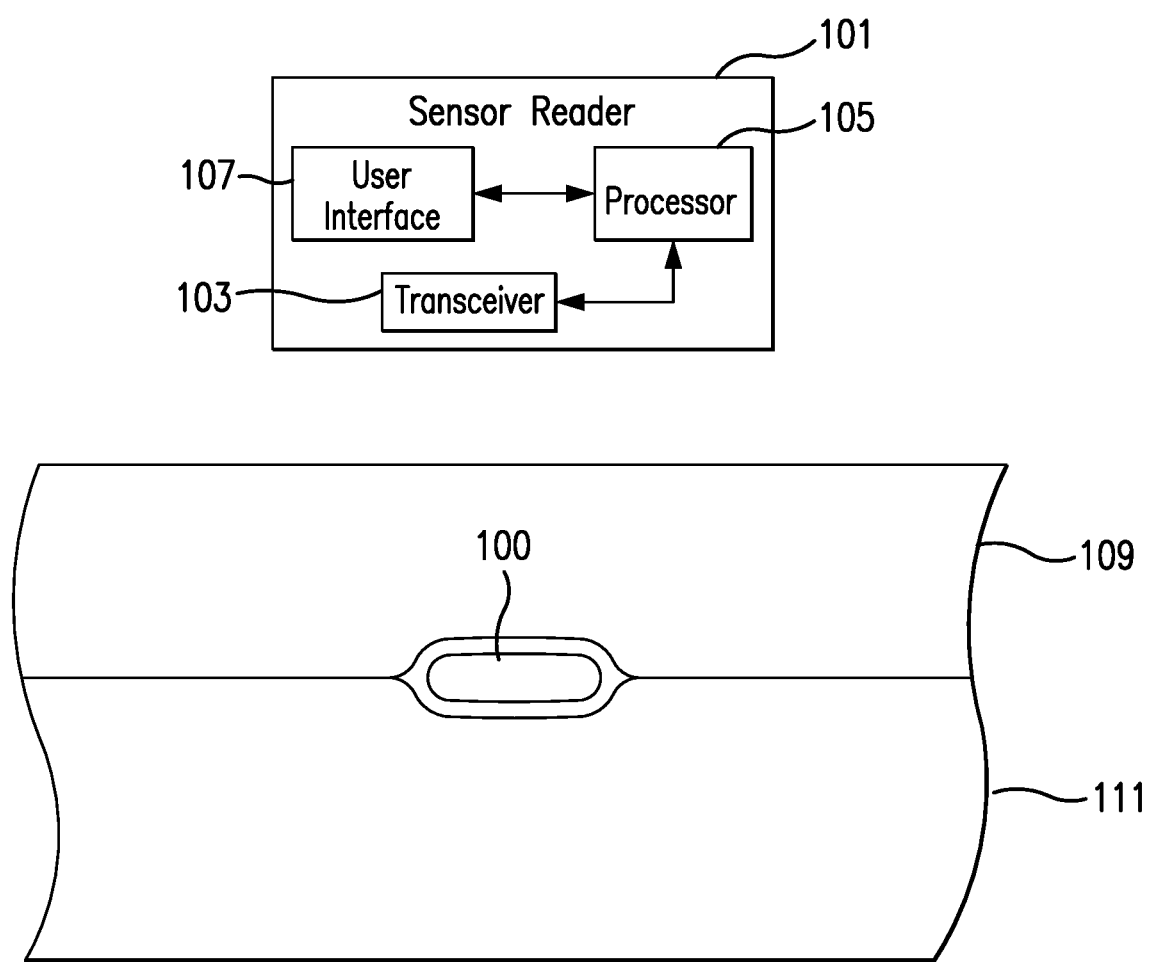
FIG. 1 is a schematic view of a sensor system, which includes an implantable sensor and a sensor reader, embodying aspects of the present invention.

FIG. 1 is a schematic view of a sensor system embodying aspects of the present invention. In one non-limiting embodiment, the system includes a sensor 100 and an external sensor reader 101. In the embodiment shown in FIG. 1, the sensor 100 is implanted in a living animal (e.g., a living human). The sensor 100 may be implanted, for example, in a living animal's arm, wrist, leg, abdomen, or other region of the living animal suitable for sensor implantation. For example, as shown in FIG. 1, in one non-limiting embodiment, the sensor 100 may be implanted between the skin 109 and subcutaneous tissues 111. In some embodiments, the sensor 100 may be an optical sensor. In some embodiments, the sensor 100 may be a chemical or biochemical sensor.

A sensor reader 101 may be an electronic device that communicates with the sensor 100 to power the sensor 100 and/or obtain analyte (e.g., glucose) readings from the sensor 100 on demand. In non-limiting embodiments, the reader 101 may be a handheld reader. In one embodiment, positioning (i.e., hovering or swiping/waiving/passing) the reader 101 within range over the sensor implant site (i.e., within proximity of the sensor 100) will cause the reader 101 to automatically convey a measurement command to the sensor 100 and receive a reading from the sensor 100. The reader 101 may subsequently be returned to a user's storage space, such as, for example, a user's purse or pocket. In other non-limiting embodiments, the reader may be stationary, for example, with a simple loop (i.e., coil) through which a user thrusts their wrist and a sensor 100 embedded therein. Thus, in such embodiments, the stationary reader could sit on a table or bathroom counter (or wherever) for occasional use by the user, and the user could, for example, wake up each morning and move their wrist through a coil while brushing their teeth.

In some embodiments, the sensor reader 101 may include a transceiver 103, a processor 105 and/or a user interface 107. In one non-limiting embodiment, the user interface 107 may include a liquid crystal display (LCD), but, in other embodiments, different types of displays may be used. In some embodiments, the transceiver 103 may include an inductive element, such as, for example, a coil. The transceiver 103 may generate an electromagnetic wave or electrodynamic field (e.g., by using a coil) to induce a current in an inductive element (e.g., inductive element 114 of FIGS. 11A-11C) of the sensor 100, which powers the sensor 100. The transceiver 103 may also convey data (e.g., commands) to the sensor 100. For example, in a non-limiting embodiment, the transceiver 103 may convey data by modulating the electromagnetic wave used to power the sensor 100 (e.g., by modulating the current flowing through a coil of the transceiver 103). The modulation in the electromagnetic wave generated by the reader 101 may be detected/extracted by the sensor 100 (e.g., by data extractor 642 of FIG. 11D). Moreover, the transceiver 103 may receive data (e.g., measurement information) from the sensor 100. For example, in a non-limiting embodiment, the transceiver 103 may receive data by detecting modulations in the electromagnetic wave generated by the sensor 100 (e.g., by clamp/modulator 646 of FIG. 11D), e.g., by detecting modulations in the current flowing through the coil of the transceiver 103.

Figure 2A:
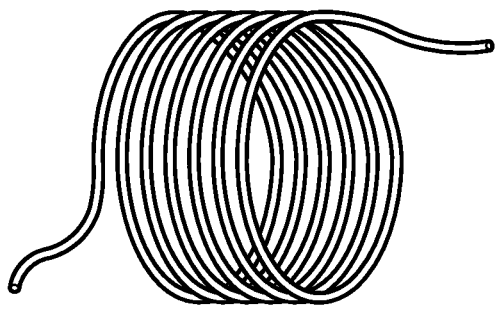
FIGS. 2A-2C illustrate example configurations of the inductive element of the external sensor reader in accordance with embodiments of the present invention.
Figure 2B:
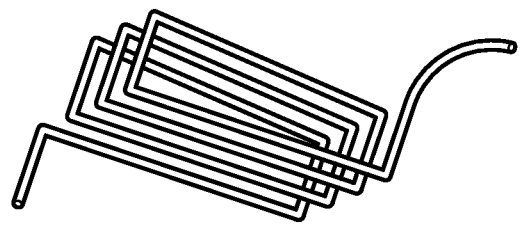
Figure 2C:
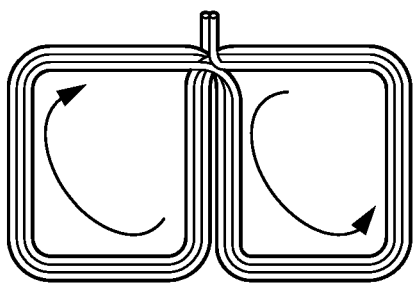

The inductive element of the transceiver 103 and the inductive element (e.g., inductive element 114 of FIGS. 11A-11C) of the sensor 100 may be in any configuration that permits adequate field strength to be achieved when the two inductive elements are brought within adequate physical proximity. The inductive element of the sensor 100 (i.e., the secondary inductive element), which may comprise a coil (e.g., coil 220 of FIG. 11D), may be contained within the sensor and may be a fixed element in alignment according to the implantation of the sensor 100. FIGS. 2A-2C illustrate examples of the inductive element of transceiver 103 (i.e., the primary inductive element), which may comprise a coil (i.e., the primary coil). FIG. 2A illustrates an example of a cylindrical coil. FIG. 2B illustrates a square or rectangular coil. FIG. 2C illustrates a FIG. 8 or planar coil. The transceiver may include a coil in any of these configurations for alignment with the coil of the sensor 100. Alternatively, the transceiver 103 may have any coil with natural field alignment vectors sufficiently coaxial with the secondary coil such that the primary and secondary coils between the reader 101 and sensor 100, respectively, can achieve adequate field strength within some physical proximity.

Figure 3:
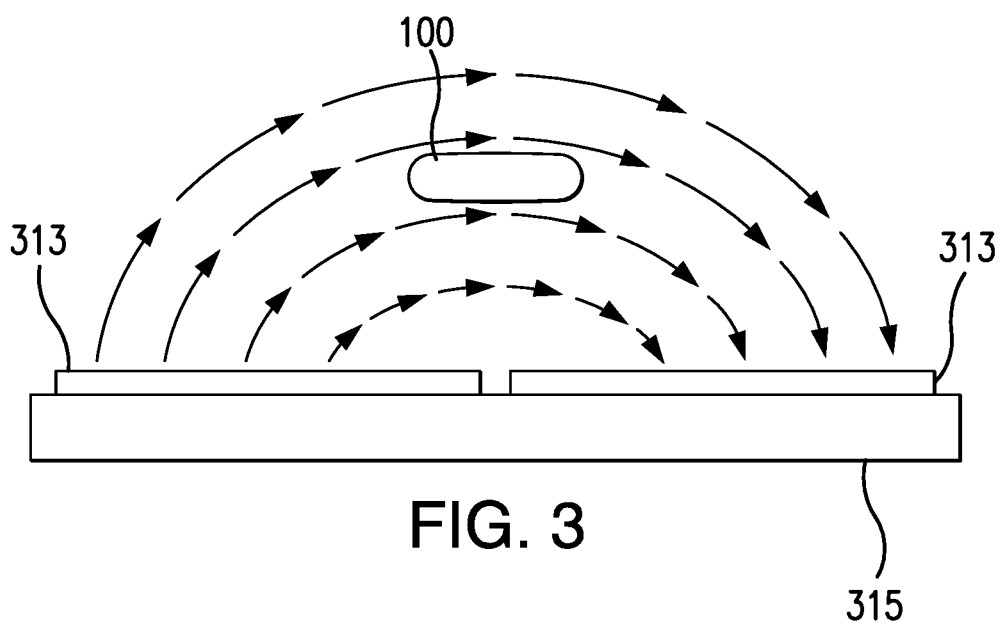
FIG. 3 illustrates a sensor in alignment with an electromagnetic field emitted by the inductive element of a transceiver in accordance with an embodiment of the present invention.

The primary coil configurations illustrated in FIGS. 2A-2C (or other suitable primary coil configuration) may or may not have ferrite cores. FIG. 3 illustrates a non-limiting embodiment of a sensor 100 in alignment with an electromagnetic field emitted by the inductive element 313 of transceiver 103. In the illustrated embodiment, the inductive element 313 is a FIG. 8 or planar coil having a substrate 315.

The sensor reader 101 may be capable of communicating with other electronic devices, like smartphones or computers. In some embodiments, the reader 101 may communicate with the sensor 100 in less than one second (e.g., in approximately 10 milliseconds), and a swiping motion of the sensor reader over the area where the sensor was inserted may, therefore, be enough to obtain a reading/measurement from the sensor 100. In some embodiments, the sensor reader 101 may then communicate with, for example, a computer, iPhone, or any other smartphone for display purposes. The sensor reader 101 may have different embodiments and different ways of communicating with other electronic devices. In one embodiment, the sensor reader 101 may be a small container or box (or any convenient form factor) carried in a bag, purse, or pocket (see FIG. 9). In another embodiment, the sensor reader 101 can be carried as a key fob or worn on a neck lanyard, or, as noted above, the sensor reader 101 might sit on a table or a bathroom counter to be operated and have a loop antenna into which a user transiently inserts a body part (e.g., wrist) into which a sensor 100 has been implanted. In these examples, the reader 101 could communicate through Bluetooth or other wireless radio standard to a smartphone or computer, or the sensor reader 101 could be physically connected to the other electronic device through a pin or cable. In some embodiments, the sensor reader 101 may be a smartphone case (see FIGS. 4A-7E). The case may contain the same electronics as the small container or box, and the case may either draw power from the phone through a port connection or it can require separate charging. The case may also communicate with the smartphone through the same port connection. To obtain a glucose reading, the user may simply swipe the encased smartphone over the sensor and the reading would be displayed, for example, in the smartphone screen.

The sensor reader may communicate with and/or power the implanted sensor, for example, through inductive coupling as described in U.S. Pat. No. 7,553,280, which is incorporated by reference herein in its entirety. In an embodiment of the present invention, the implanted sensor 100 is passive and the sensor reader 101 powers the sensor 100 through inductive coupling. In one non-limiting embodiment, the internal sensor unit 100 may include a secondary coil forming part of a power supply for the sensor unit, a load coupled to said secondary coil, and a sensor circuit for modifying said load in accordance with sensor measurement information obtained by the sensor circuit. The swipe reader 101 may include a primary coil that is mutually inductively coupled to the secondary coil upon the primary coil coming into a predetermined proximity distance from said secondary coil, an oscillator for driving said primary coil to induce a charging current in said secondary coil, and a detector for detecting variations in a load on the primary coil induced by changes to the load in the internal sensor unit and for providing information signals corresponding to the load changes.

In some non-limiting embodiments, the inductive element of the transceiver 103 of the reader 101 may be a coil contained within an adaptable reader device, such as a smartphone or tablet (see FIG. 10), or the inductive element of the transceiver 103 may be a part of an adapter or an add-on to such a device (see FIG. 8), such as a cover for a smart phone type handheld (see FIGS. 4A-7E), or a piggyback design connected by wireless protocol or cable, or may be included in the design and construction of a dedicated reader device (see FIG. 9) such as a smart phone, dedicated handheld reader, wand, or adapter that will enable triggered readings of an implanted sensor during transient proximal motion within range.

In some embodiments, the processor 105 may output to the transceiver 103 the data to be conveyed to the sensor 100 and may receive from the transceiver 103 the data received from the sensor 100. In one embodiment, the processor 105 may serialize and encode the data to be conveyed to the sensor 100 before outputting it to the transceiver 103 for transmission. Similarly, the processor 105 may decode and/or serialize the data received from the sensor 100. In some embodiments, the data received from the sensor 100 may be measurement information, and the processor 105 may process the measurement information to determine a concentration of an analyte. However, in other embodiments, the sensor 100 may process the measurement information to determine a concentration of an analyte, and the data received from the sensor 100 may be the determined concentration of the analyte. In some embodiments, the processor 105 may cause the user interface 107 to display a value representing the concentration of the analyte so that a user (e.g., the patient, a doctor and/or others) can read the value. Also, in some embodiments, the processor 105 may receive from the user interface 107 user input (e.g., a user request for a sensor reading, such as the concentration of an analyte). Furthermore, in some embodiments, the sensor reader 101 may include one or more input/output ports that enable transmission of data (e.g., traceability information and/or measurement information) and receipt of data (e.g., sensor commands and/or setup parameters) between the sensor reader 101 and another device (e.g., a computer and/or smartphone).

Figure 4:
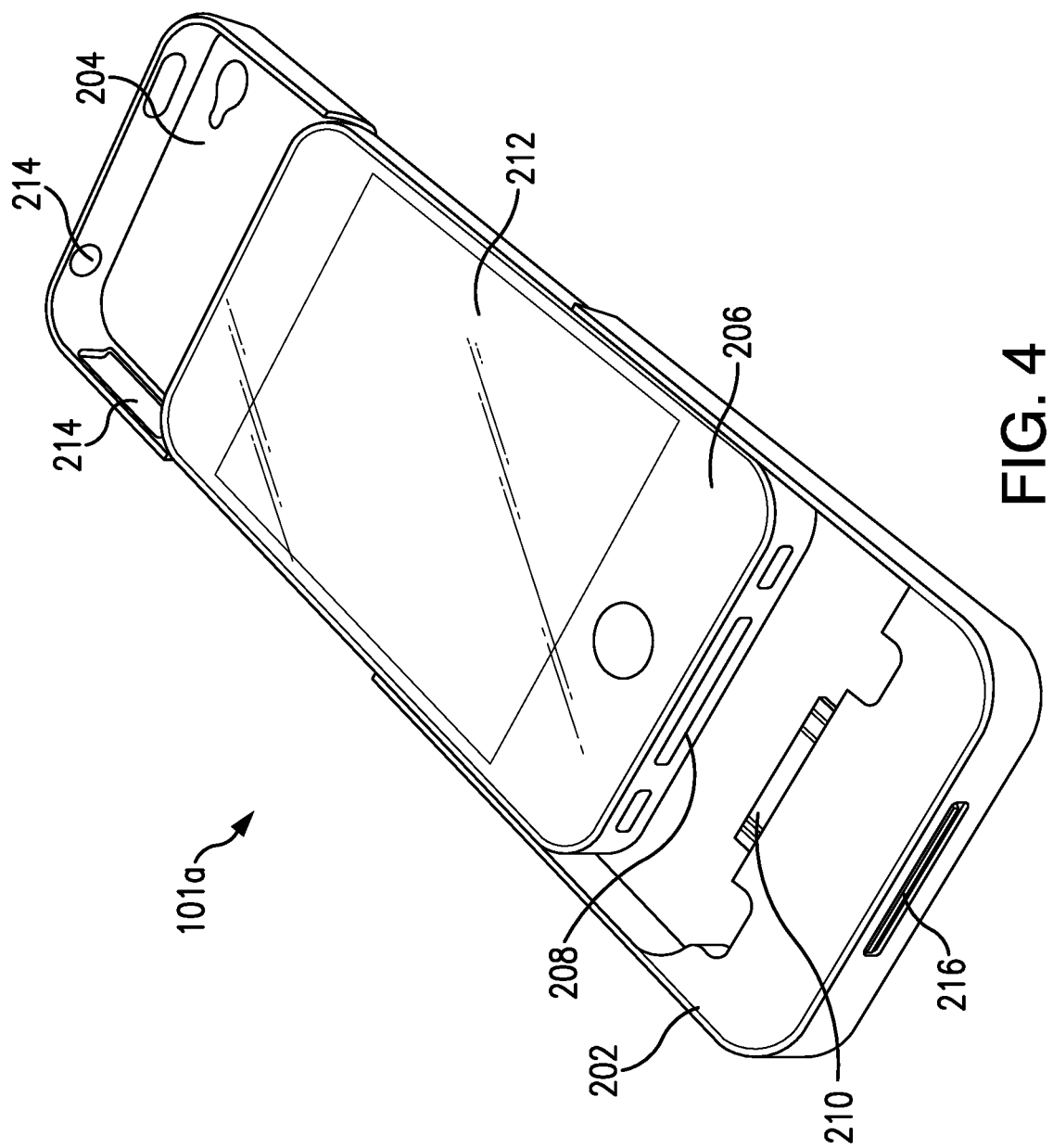
Figure 5A:
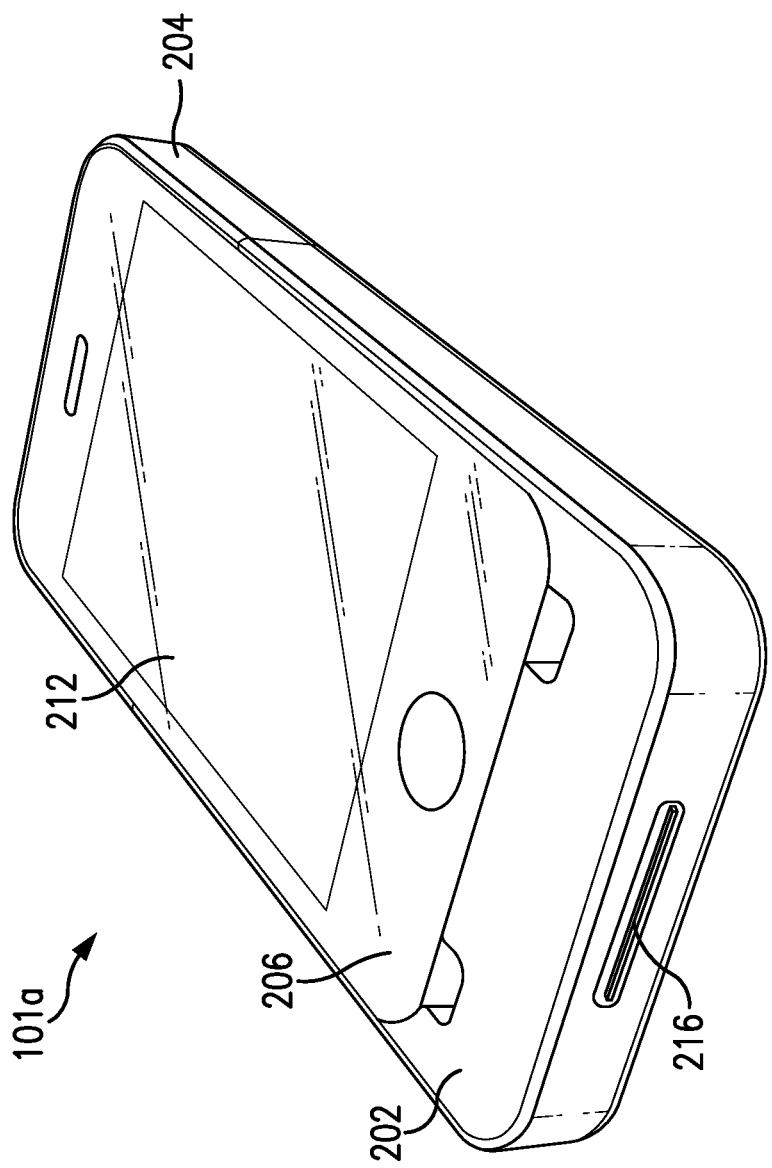
FIGS. 5A and 5B illustrate perspective and side views, respectively, of the sensor reader with the smartphone case encasing the smartphone in accordance with an embodiment of the present invention.
Figure 5B:
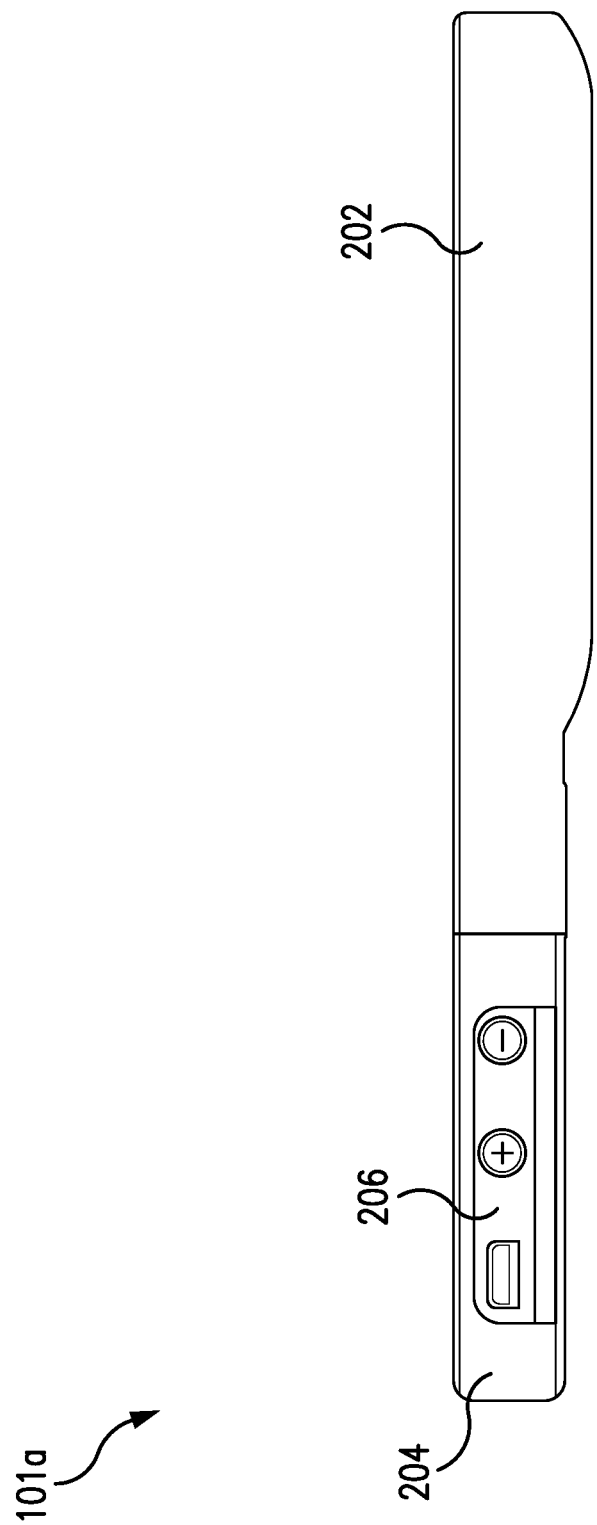
Figure 6:
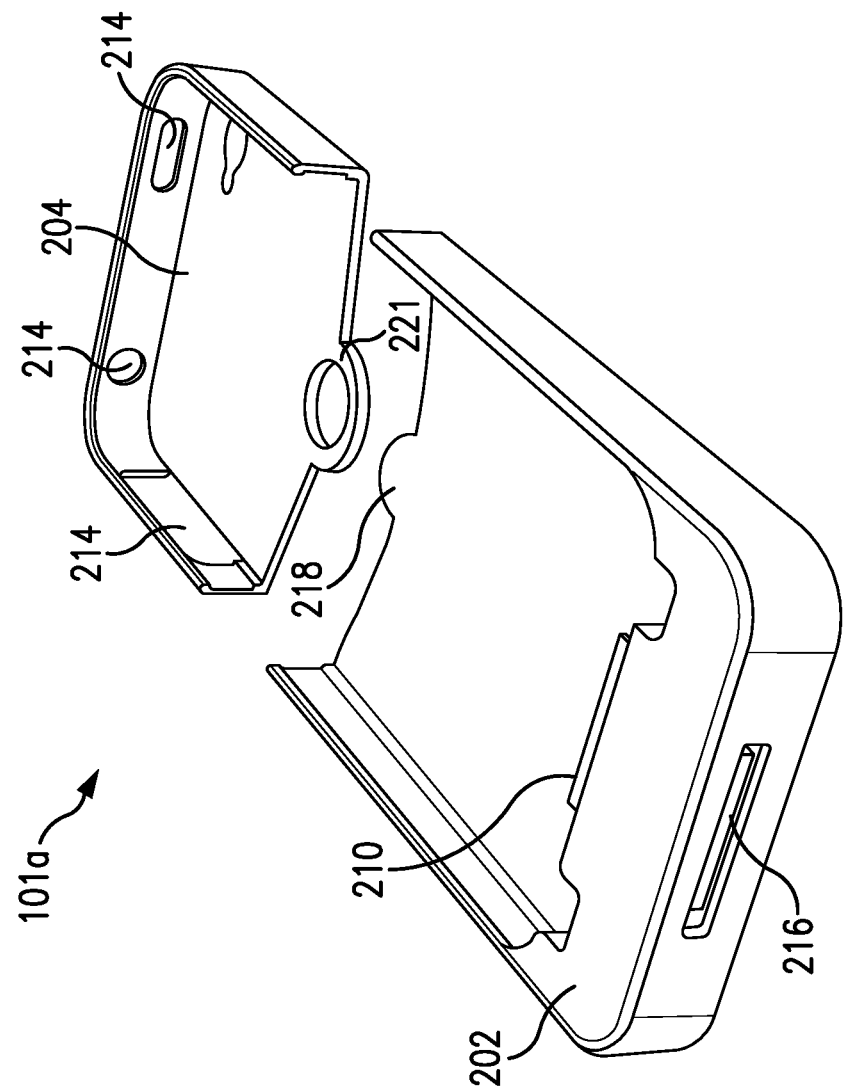
Figure 7:
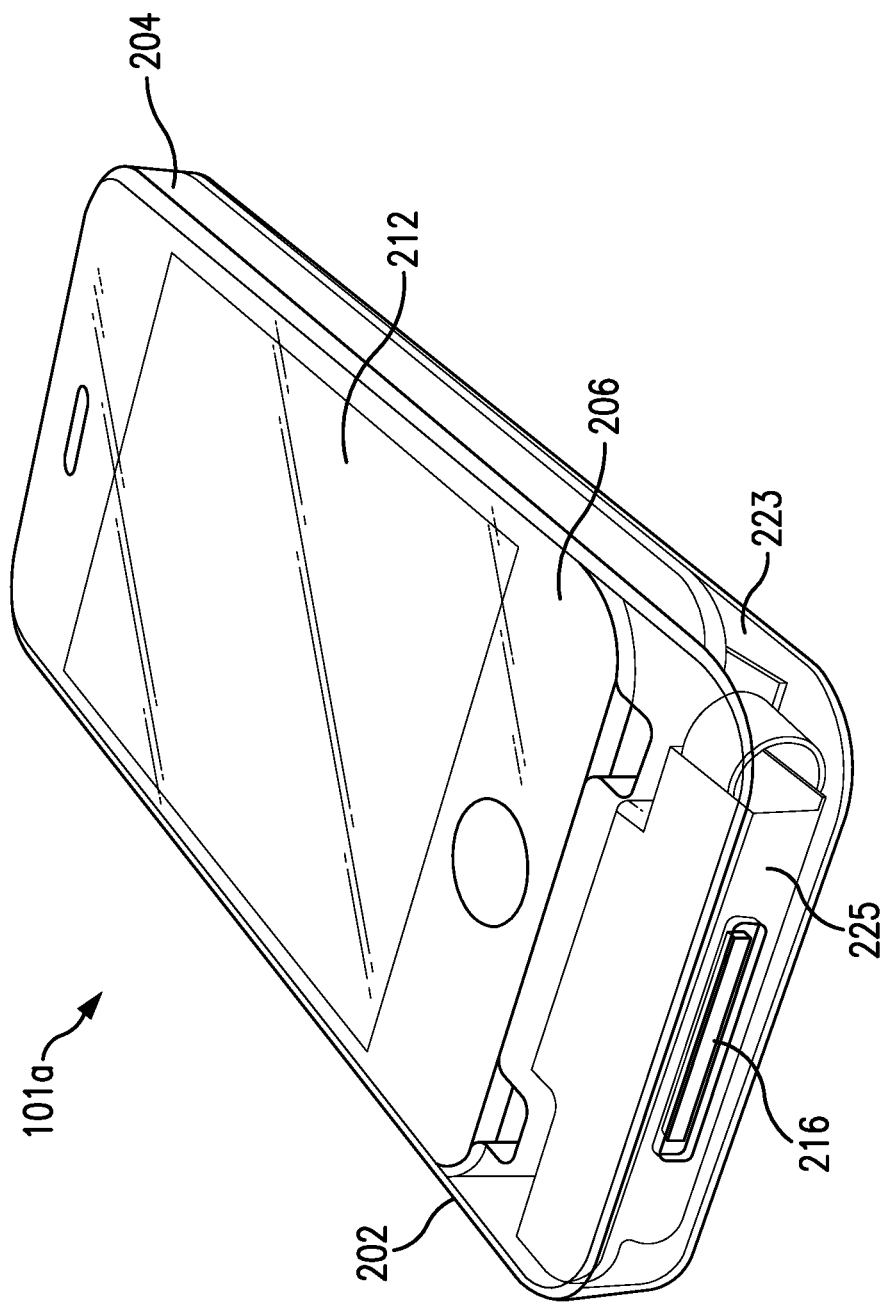

FIGS. 4-7 illustrate a non-limiting embodiment of an external sensor reader 101a that includes a smartphone 206 and an adapter in the form of a smartphone case. FIG. 4 illustrates a perspective view of an exploded sensor reader 101a. FIGS. 5A and 5B illustrate perspective and side views, respectively, of the sensor reader 101a with the smartphone case encasing the smartphone 206. FIG. 6 illustrates a perspective view of the smartphone case of the sensor reader 101a without the smartphone 206. FIG. 7 illustrates a perspective view of the sensor reader 101a with the smartphone case encasing the smartphone 206 and the bottom casing 202 shown as transparent.

The smartphone 206 may act as the user interface (see user interface 107 of FIG. 1) of sensor reader 101a. In addition, the smartphone 206 may provide none, some, or all of the processing functionality (see processor 105 of FIG. 1) of the sensor reader 101a. The smartphone case may have reading components 225 that may act as the transceiver (see transceiver 103 of FIG. 1) and may provide none, some, or all of the processing functionality (see processor 105 of FIG. 1) of the sensor reader 101a.

The sensor reader 101a may be configured to read and/or power an internal sensor (e.g., sensor 100) when swiped or moved within a maximum distance, e.g., one inch, of the internal sensor. The smartphone case may include a bottom casing 202 and a top casing 204. The bottom casing 202 and top casing 204 may be configured to encase the smartphone 206. In some embodiments, the smartphone 206 may include a port 208, and the bottom casing 202 may include a coupling member or pin 210 configured to be inserted into and couple with the port 208 of the smartphone 206. The smartphone casing may be configured such that, when the pin 210 of bottom casing 202 is coupled with the port 208 of the smartphone 206, the smartphone casing and the smartphone 206 can communicate with each other. Additionally or alternatively, the smartphone casing may be configured such that, when the pin 210 of bottom casing 202 is coupled with the port 208 of the smartphone 206, the smartphone 206 supplies power to the sensor reader 101a via the port connection, i.e., via the pin 210 being inserted into the port 208.

In some embodiments of the present invention, the smartphone 206 may include a display 212. The display 212 can be configured to display the analyte (e.g., glucose) measurements obtained from sensor 100. In some embodiments of the present invention, the top casing 204 may include openings 214 configured to allow the interactive and functional features of the smartphone 206 (e.g., volume control, power button, and/or audio ports) to remain unobstructed when the smartphone casing encases the smartphone 206. In some non-limiting embodiments, the bottom casing 202 may include a port 216 configured to receive a pin. The bottom casing port 216 can be used to communicate information to another electronic device (e.g., a computer or different smartphone). In some embodiments, the port 216 may also be used to allow electronic devices to communicate with the smartphone 206.

In some embodiments of the present invention, the bottom casing 202 may include a coupling member 218, and the top casing 204 may include a coupling member 221 (see FIG. 6). The coupling members 218 and 221 may be configured to couple such that the bottom casing 202 and the top casing 204 encase the smartphone 206. In a non-limiting embodiment of the present invention, the bottom casing coupling member 218 may be a protrusion, and the top casing coupling member 221 may be an opening configured to receive the bottom casing coupling member 218. The coupling members 218 and 221 may be configured to allow a user to couple and decouple the casing from the smartphone 206 (i.e., the coupling members 218 and 221 do not permanently couple).

In some embodiments, the bottom casing 202 may include the circuitry and components for reading the sensor 100. The bottom casing 202 may include a housing 223 and reading components 225, as illustrated in FIG. 7. The reading components may include an inductive element (e.g., a coil), an oscillator, and/or a detector. Such reading components are described in further detail in U.S. Pat. No. 7,553,280, which is incorporated by reference herein in its entirety. In a non-limiting embodiment of the present invention, the bottom casing 202 may additionally include a power source, such as a battery.

Figure 8:
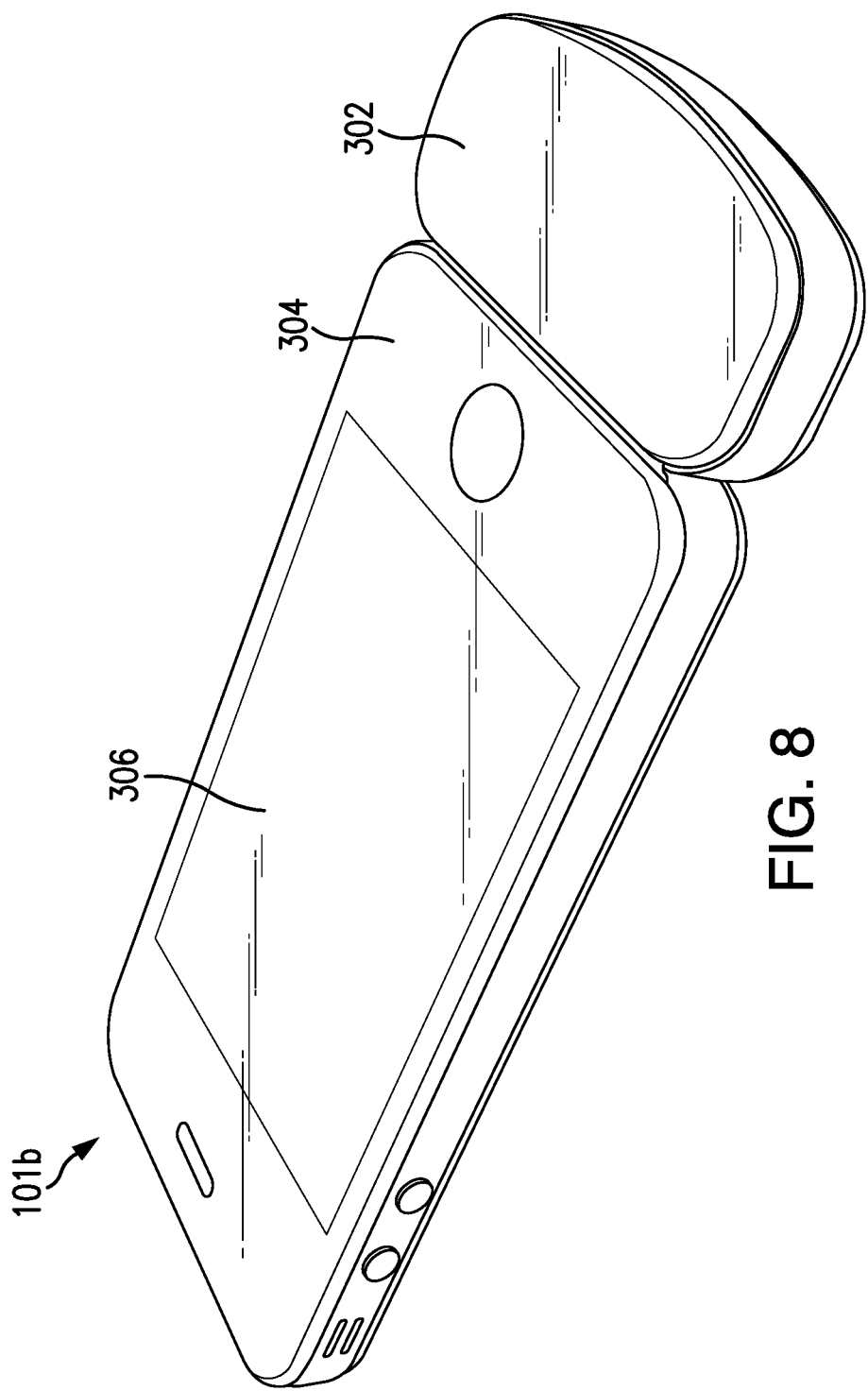
FIG. 8 illustrates an external sensor reader that includes a smartphone and an adapter in accordance with an embodiment of the present invention.

FIG. 8 illustrates a non-limiting embodiment of an external sensor reader 101b that includes a smartphone 304 and an adapter 302. Unlike the adapter of sensor reader 101a, the adapter 302 of sensor reader 101b is not in the form of a smartphone case. The adapter 302 of sensor reader 101b may be configured to couple to a smartphone 304. The adapter 302 may include a pin, as described above (see pin 210 of FIGS. 4A, 4E, 6A, and 6B), configured to couple with a port of the smartphone 304. The adapter 302 may include reading components (see reading components 225 of FIGS. 7A-7E) configured to read and/or power an internal sensor. The smartphone 304 can include a display 306, which can display the analyte values obtained from the sensor.

Figure 9:
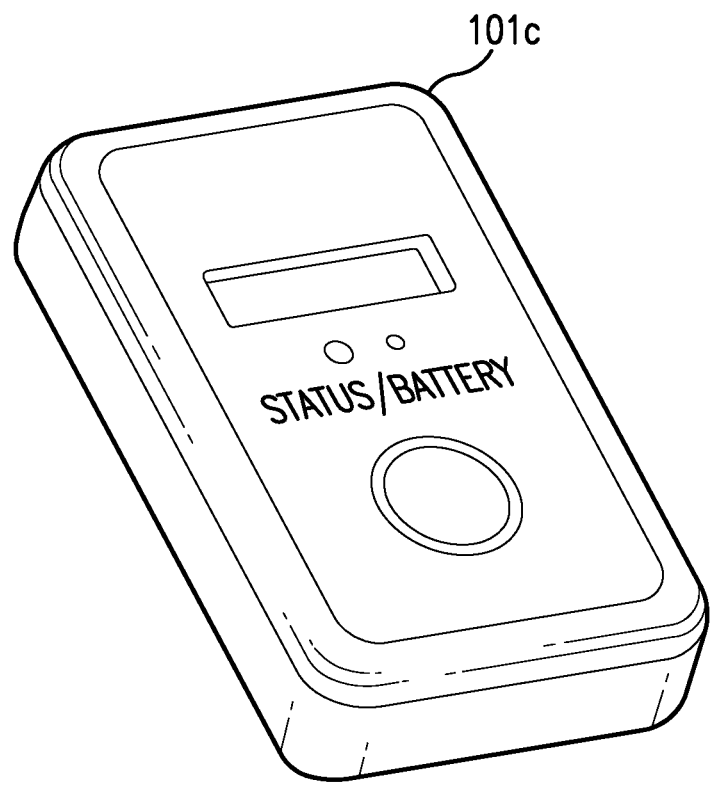
FIG. 9 illustrates an external sensor reader that is a dedicated reader device in accordance with an embodiment of the present invention.

FIG. 9 illustrates a non-limiting embodiment of an external sensor reader 101c that is a dedicated reader device, such as a smart phone, dedicated handheld reader, wand, or adapter, that will enable triggered readings of an implanted sensor 100 during transient proximal motion within range. The dedicated reader device may act as the user interface (see user interface 107 of FIG. 1) and transceiver (see transceiver 103 of FIG. 1) of sensor reader 101c and may provide all of the processing functionality (see processor 105 of FIG. 1) of the sensor reader 101c. Furthermore, in a non-limiting embodiment, the sensor reader 101c may include one or more input/output ports that enable transmission (e.g., via wireless radio technology, such as Bluetooth low energy) of and receipt of data (e.g., sensor commands and/or setup parameters) between the sensor reader 101 and another device (e.g., a computer and/or smartphone).

Figure 10:
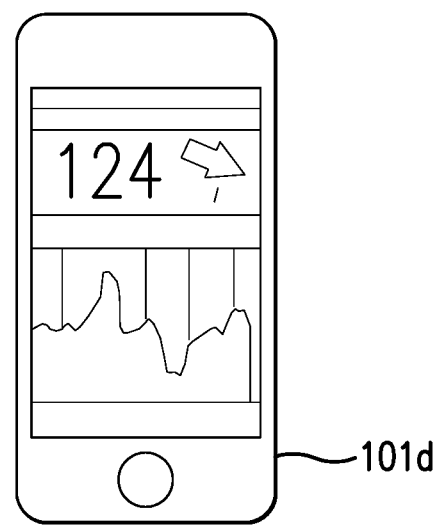
FIG. 10 illustrates an external sensor reader that is an adaptable reader device in accordance with an embodiment of the present invention.

FIG. 10 illustrates a non-limiting embodiment of an external sensor reader 101d that is an adaptable reader device, such as a smartphone or tablet, having an inductive element (e.g., a coil) contained within the adaptable reader device. The adaptable reader device may act as the user interface (see user interface 107 of FIG. 1) and transceiver (see transceiver 103 of FIG. 1) of sensor reader 101d and may provide all of the processing functionality (see processor 105 of FIG. 1) of the sensor reader 101d.

Figure 11A:
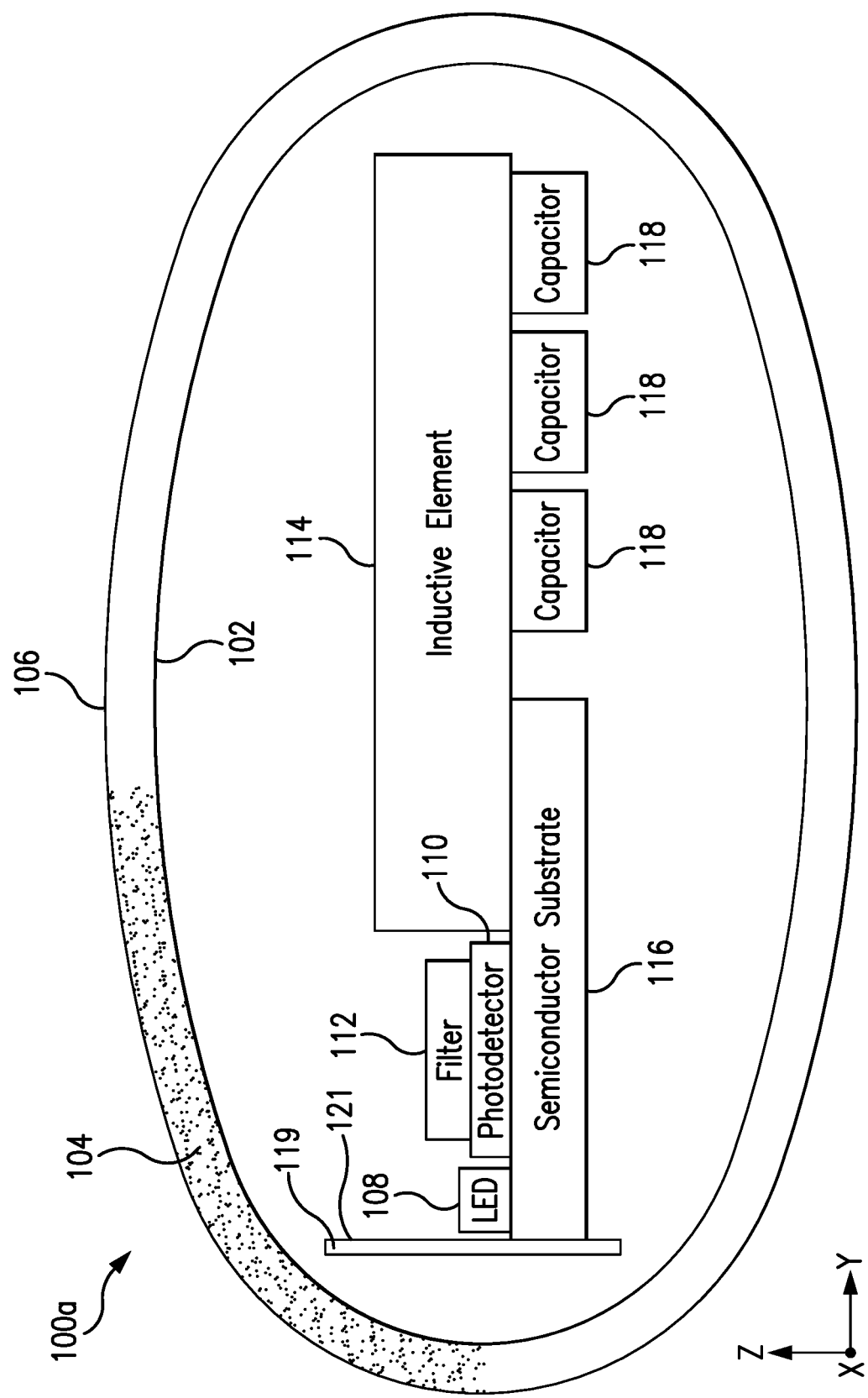
FIG. 11A is a schematic, section view illustrating a sensor embodying aspects of the present invention.

FIG. 11A is a schematic, section view of a sensor 100a, which is an embodiment of the sensor embodying aspects of the present invention. In some embodiments, the sensor 100 may be an optical sensor. In one non-limiting embodiment, sensor 100 includes a sensor housing 102. In exemplary embodiments, sensor housing 102 may be formed from a suitable, optically transmissive polymer material, such as, for example, acrylic polymers (e.g., polymethylmethacrylate (PMMA)).

In the embodiment illustrated in FIG. 11A, the sensor 100 includes indicator molecules 104. Indicator molecules 104 may be fluorescent indicator molecules or absorption indicator molecules. In some non-limiting embodiments, sensor 100 may include a matrix layer 106 coated on at least part of the exterior surface of the sensor housing 102, with the indicator molecules 104 distributed throughout the matrix layer 106. The matrix layer 106 may cover the entire surface of sensor housing 102 or only one or more portions of the surface of housing 102. Similarly, the indicator molecules 104 may be distributed throughout the entire matrix layer 106 or only throughout one or more portions of the matrix layer 106. Furthermore, as an alternative to coating the matrix layer 106 on the outer surface of sensor housing 102, the matrix layer 106 may be disposed on the outer surface of the sensor housing 102 in other ways, such as by deposition or adhesion.

In the embodiment illustrated in FIG. 11A, the sensor 100 includes a light source 108, which may be, for example, a light emitting diode (LED) or other light source, that emits radiation, including radiation over a range of wavelengths that interact with the indicator molecules 104.

In the embodiment illustrated in FIG. 11A, sensor 100 also includes one or more photodetectors 110 (e.g., photodiodes, phototransistors, photoresistors or other photosensitive elements) which, in the case of a fluorescence-based sensor, is sensitive to fluorescent light emitted by the indicator molecules 104 such that a signal is generated by the photodetector 110 in response thereto that is indicative of the level of fluorescence of the indicator molecules and, thus, the amount of analyte of interest (e.g., glucose).

As illustrated in FIG. 11A, some embodiments of sensor 100 include one or more optical filters 112, such as high pass or band pass filters, that may cover a photosensitive side of the one or more photodetectors 110.

As shown in FIG. 11A, in some embodiments, sensor 100 may be wholly self-contained. In other words, the sensor may be constructed in such a way that no electrical leads extend into or out of the sensor housing 102 to supply power to the sensor (e.g., for driving the light source 108) or to convey signals from the sensor 100. Instead, in one embodiment, sensor 100 may be powered by an external power source (e.g., external sensor reader 101). For example, the external power source may generate a magnetic field to induce a current in an inductive element 114 (e.g., a coil or other inductive element). Additionally, the sensor 100 may use the inductive element 114 to communicate information to an external data reader (not shown). In some embodiments, the external power source and data reader may be the same device.

In some embodiments, sensor 100 includes a semiconductor substrate 116. In the embodiment illustrated in FIG. 11A, circuitry is fabricated in the semiconductor substrate 116. The circuitry may include analog and/or digital circuitry. Also, although in some preferred embodiments the circuitry is fabricated in the semiconductor substrate 116, in alternative embodiments, a portion or all of the circuitry may be mounted or otherwise attached to the semiconductor substrate 116. In other words, in alternative embodiments, a portion or all of the circuitry may include discrete circuit elements, an integrated circuit (e.g., an application specific integrated circuit (ASIC)) and/or other electronic components discrete and may be secured to the semiconductor substrate 116, which may provide communication paths between the various secured components.

In some embodiments, the one or more photodetectors 110 may be mounted on the semiconductor substrate 116, but, in some preferred embodiments, the one or more photodetectors 110 may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

As shown in the embodiment illustrated in FIG. 11A, in some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, the sensor 100 may include a reflector (i.e., mirror) 119. As shown in FIG. 11A, reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from entering the axial end of the sensor 100.

According to one aspect of the invention, an application for which the sensor 100 was developed—although by no means the only application for which it is suitable—is measuring various biological analytes in the living body of an animal (including a human). For example, sensor 110 may be used to measure glucose, oxygen, toxins, pharmaceuticals or other drugs, hormones, and other metabolic analytes in, for example, the human body. The specific composition of the matrix layer 104 and the indicator molecules 106 may vary depending on the particular analyte the sensor is to be used to detect and/or where the sensor is to be used to detect the analyte (i.e., in the blood or in subcutaneous tissues). Preferably, however, matrix layer 104, if present, should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

Figure 11B:
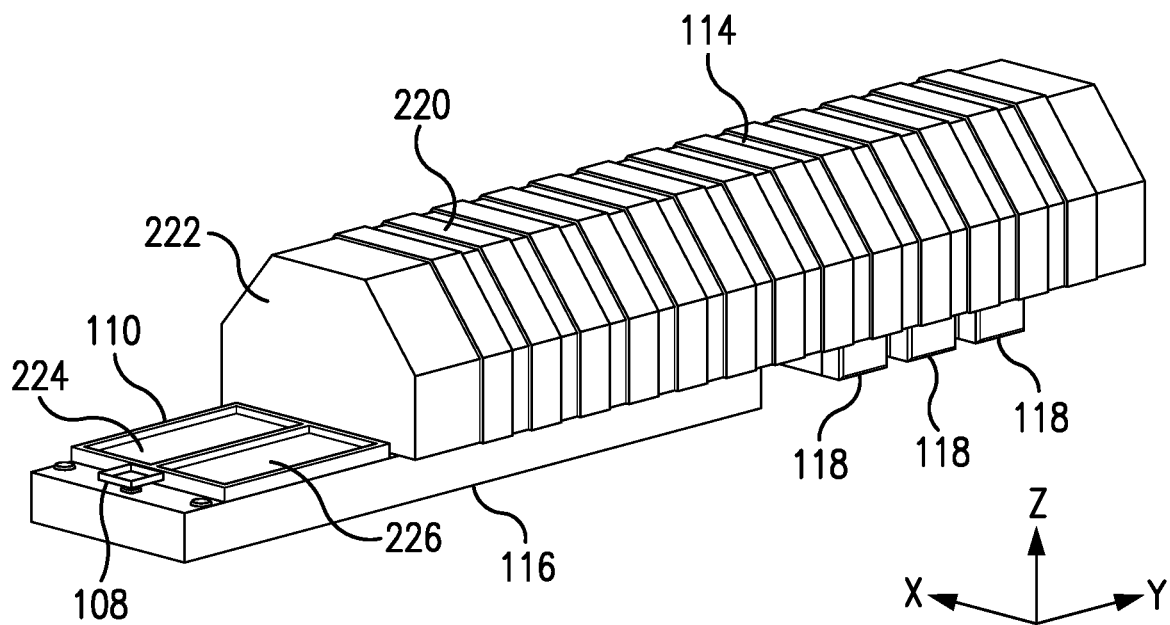
FIGS. 11B and 11C illustrate perspective views of a sensor embodying aspects of the present invention.
Figure 11C:
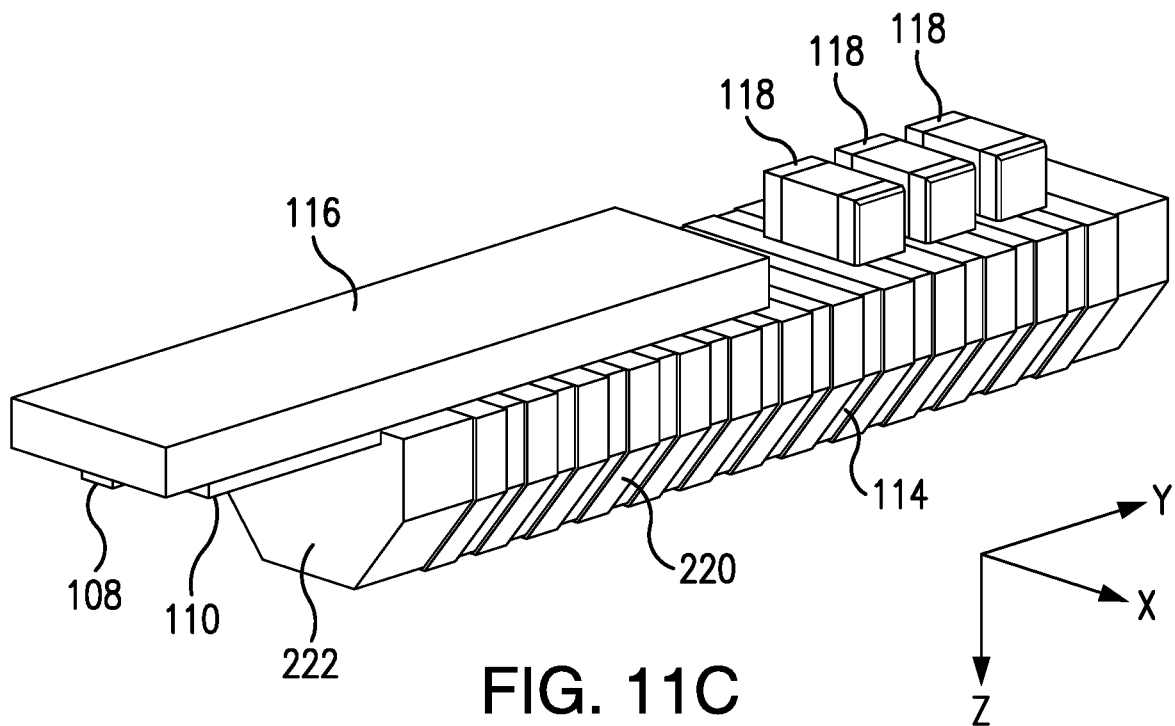

FIGS. 11B and 11C illustrate perspective views of the sensor 100. In FIGS. 11B and 11C, the reflector 119, which may be included in some embodiments of the sensor 100, is not illustrated. In the embodiment illustrated in FIGS. 11B and 11C, the inductive element 114 comprises a coil 220. In one embodiment, coil 220 may be a copper coil but other conductive materials, such as, for example, screen printed gold, may alternatively be used. In some embodiments, the coil 220 is formed around a ferrite core 222. Although core 222 is ferrite in some embodiments, in other embodiments, other core materials may alternatively be used. In some embodiments, coil 220 is not formed around a core. Although coil 220 is illustrated as a cylindrical coil in FIGS. 11B and 11C, in other embodiments, coil 220 may be a different type of coil, such as, for example, a flat coil.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which is important for implant applications, and increases cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the embodiment illustrated in FIGS. 11B and 11C, the one or more photodetectors 110 include a first photodetector 224 and a second photodetector 226. First and second photodetectors 224 and 226 may be mounted on or fabricated in the semiconductor substrate 116. In the embodiment illustrated in FIGS. 11B and 11C, sensor 100 may include one or more optical filters 112 even though they are not shown.

Figure 11D:
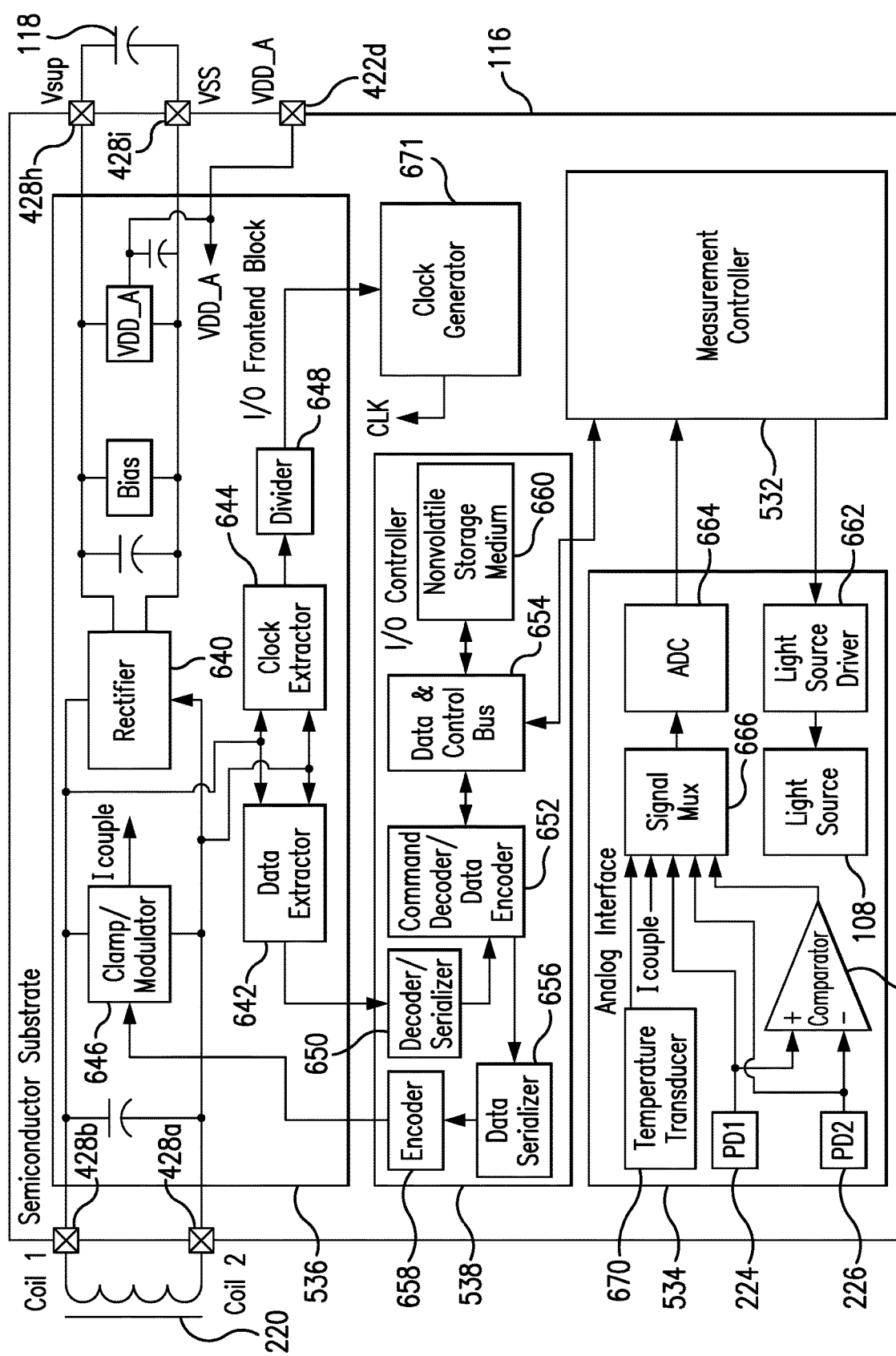
FIG. 11D is block diagram illustrating the functional blocks of the circuitry of a sensor according to an embodiment in which the circuitry is fabricated in the semiconductor substrate.

FIG. 11D is block diagram illustrating the functional blocks of the circuitry of sensor 100 according to a non-limiting embodiment in which the circuitry is fabricated in the semiconductor substrate 116. As shown in the embodiment of FIG. 11D, in some embodiments, an input/output (I/O) frontend block 536 may be connected to the external inductive element 114, which may be in the form of a coil 220, through coil contacts 428a and 428b. The I/O frontend block 536 may include a rectifier 640, a data extractor 642, a clock extractor 644, clamp/modulator 646 and/or frequency divider 648. Data extractor 642, clock extractor 644 and clamp/modulator 646 may each be connected to external coil 220 through coil contacts 428a and 428b. The rectifier 640 may convert an alternating current produced by coil 220 to a direct current that may be used to power the sensor 100. For instance, the direct current may be used to produce one or more voltages, such as, for example, voltage VDD_A, which may be used to power the one or more photodetectors 110. In one non-limiting embodiment, the rectifier 640 may be a Schottky diode; however, other types of rectifiers may be used in other embodiments. The data extractor 642 may extract data from the alternating current produced by coil 220. The clock extractor 644 may extract a signal having a frequency (e.g., 13.56 MHz) from the alternating current produced by coil 220. The frequency divider 648 may divide the frequency of the signal output by the clock extractor 644. For example, in a non-limiting embodiment, the frequency divider 648 may be a 4:1 frequency divider that receives a signal having a frequency (e.g., 13.56 MHz) as an input and outputs a signal having a frequency (e.g., 3.39 MHz) equal to one fourth the frequency of the input signal. The outputs of rectifier 640 may be connected outputs of rectifier 640 may be connected to one or more external capacitors 118 (e.g., one or more regulation capacitors) through contacts 428h and 428i.

In some embodiments, an I/O controller 538 may include a decoder/serializer 650, command decoder/data encoder 652, data and control bus 654, data serializer 656 and/or encoder 658. The decoder/serializer 650 may decode and serialize the data extracted by the data extractor 642 from the alternating current produced by coil 220. The command decoder/data encoder 652 may receive the data decoded and serialized by the decoder/serializer 650 and may decode commands therefrom. The data and control bus 654 may receive commands decoded by the command decoder/data encoder 652 and transfer the decoded commands to the measurement controller 532. The data and control bus 654 may also receive data, such as measurement information, from the measurement controller 532 and may transfer the received data to the command decoder/data encoder 652. The command decoder/data encoder 652 may encode the data received from the data and control bus 654. The data serializer 656 may receive encoded data from the command decoder/data encoder 652 and may serialize the received encoded data. The encoder 658 may receive serialized data from the data serializer 656 and may encode the serialized data. In a non-limiting embodiment, the encoder 658 may be a Manchester encoder that applies Manchester encoding (i.e., phase encoding) to the serialized data. However, in other embodiments, other types of encoders may alternatively be used for the encoder 658, such as, for example, an encoder that applies 8B/10B encoding to the serialized data.

The clamp/modulator 646 of the I/O frontend block 536 may receive the data encoded by the encoder 658 and may modulate the current flowing through the inductive element 114 (e.g., coil 220) as a function of the encoded data. In this way, the encoded data may be conveyed wirelessly by the inductive element 114 as a modulated electromagnetic wave. The conveyed data may be detected by an external reading device by, for example, measuring the current induced by the modulated electromagnetic wave in a coil of the external reading device. Furthermore, by modulating the current flowing through the coil 220 as a function of the encoded data, the encoded data may be conveyed wirelessly by the coil 220 as a modulated electromagnetic wave even while the coil 220 is being used to produce operating power for the sensor 100. See, for example, U.S. Pat. Nos. 6,330,464 and 8,073,548, which are incorporated herein by reference in their entireties and which describe a coil used to provide operative power to an optical sensor and to wirelessly convey data from the optical sensor. In some embodiments, the encoded data is conveyed by the sensor 100 using the clamp/modulator 646 at times when data (e.g., commands) are not being received by the sensor 100 and extracted by the data extractor 642. For example, in one non-limiting embodiment, all commands may be initiated by an external sensor reader (e.g., sensor 1500 of FIG. 15) and then responded to by the sensor 100 (e.g., after or as part of executing the command). In some embodiments, the communications received by the inductive element 114 and/or the communications conveyed by the inductive element 114 may be radio frequency (RF) communications. Although, in the illustrated embodiments, the sensor 100 includes a single coil 220, alternative embodiments of the sensor 100 may include two or more coils (e.g., one coil for data transmission and one coil for power and data reception).

In an embodiment, the I/O controller 538 may also include a nonvolatile storage medium 660. In a non-limiting embodiment, the nonvolatile storage medium 660 may be an electrically erasable programmable read only memory (EEPROM). However, in other embodiments, other types of nonvolatile storage media, such as flash memory, may be used. The nonvolatile storage medium 660 may receive write data (i.e., data to be written to the nonvolatile storage medium 660) from the data and control bus 654 and may supply read data (i.e., data read from the nonvolatile storage medium 660) to the data and control bus 654. In some embodiments, the nonvolatile storage medium 660 may have an integrated charge pump and/or may be connected to an external charge pump. In some embodiments, the nonvolatile storage medium 660 may store identification information (i.e., traceability or tracking information), measurement information and/or setup parameters (i.e., calibration information). In one embodiment, the identification information may uniquely identify the sensor 100. The unique identification information may, for example, enable full traceability of the sensor 100 through its production and subsequent use. In one embodiment, the nonvolatile storage medium 660 may store calibration information for each of the various sensor measurements.

In some embodiments, the analog interface 534 may include a light source driver 662, analog to digital converter (ADC) 664, a signal multiplexer (MUX) 666 and/or comparator 668. In a non-limiting embodiment, the comparator 668 may be a transimpedance amplifier, in other embodiments, different comparators may be used. The analog interface 534 may also include light source 108, one or more photodetectors 110 (e.g., first and second photodetectors 224 and 226) and/or a temperature transducer 670. In a non-limiting, exemplary embodiment, the temperature transducer 670 may be a band-gap based temperature transducer. However, in alternative embodiments, different types of temperature transducers may be used, such as, for example, thermistors or resistance temperature detectors. Furthermore, like the light source 108 and one or more photodetectors 110, in one or more alternative embodiments, the temperature transducer 670 may be mounted on semiconductor substrate 116 instead of being fabricated in semiconductor substrate 116.

The light source driver 662 may receive a signal from the measurement controller 532 indicating the light source current at which the light source 108 is to be driven, and the light source driver 662 may drive the light source 108 accordingly. The light source 108 may emit radiation from an emission point in accordance with a drive signal from the light source driver 662. The radiation may excite indicator molecules 104 distributed throughout a matrix layer 106 coated on at least part of the exterior surface of the sensor housing 102. The one or more photodetectors 110 (e.g., first and second photodetectors 224 and 226) may each output an analog light measurement signal indicative of the amount of light received by the photodetector. For instance, in the embodiment illustrated in FIG. 11D, the first photodetector 224 may output a first analog light measurement signal indicative of the amount of light received by the first photodetector 224, and the second photodetector 226 may output a first analog light measurement signal indicative of the amount of light received by the second photodetector 226. The comparator 668 may receive the first and second analog light measurement signals from the first and second photodetectors 224 and 226, respectively, and output an analog light difference measurement signal indicative of the difference between the first and second analog light measurement signals. The temperature transducer 670 may output an analog temperature measurement signal indicative of the temperature of the sensor 100. The signal MUX 666 may select one of the analog temperature measurement signal, the first analog light measurement signal, the second analog light measurement signal and the analog light difference measurement signal and may output the selected signal to the ADC 664. The ADC 664 may convert the selected analog signal received from the signal MUX 666 to a digital signal and supply the digital signal to the measurement controller 532. In this way, the ADC 664 may convert the analog temperature measurement signal, the first analog light measurement signal, the second analog light measurement signal and the analog light difference measurement signal to a digital temperature measurement signal, a first digital light measurement signal, a second digital light measurement signal and a digital light difference measurement signal, respectively, and may supply the digital signals, one at a time, to the measurement controller 532.

In some embodiments, the circuitry of sensor 100 fabricated in the semiconductor substrate 116 may additionally include a clock generator 671. The clock generator 671 may receive, as an input, the output of the frequency divider 648 and generate a clock signal CLK. The clock signal CLK may be used by one or more components of one or more of the I/O fronted block 536, I/O controller 538, measurement controller 532 and analog interface 534.

In a non-limiting embodiment, data (e.g., decoded commands from the command decoder/data encoder 652 and/or read data from the nonvolatile storage medium 660) may be transferred from the data and control bus 654 of the I/O controller 538 to the measurement controller 532 via transfer registers and/or data (e.g., write data and/or registration information) may be transferred from the measurement controller 532 to the data and control bus 654 of the I/O controller 538 via the transfer registers.

In some embodiments, the circuitry of sensor 100 may include a field strength measurement circuit. In embodiments, the field strength measurement circuit may be part of the I/O front end block 536, I/O controller 538, or the measurement controller 532 or may be a separate functional component. The field strength measurement circuit may measure the received (i.e., coupled) power (e.g., in mWatts). The field strength measurement circuit of the sensor 100 may produce a coupling value proportional to the strength of coupling between the inductive element 114 of the sensor 100 and the inductive element of the external reader 101. For example, in non-limiting embodiments, the coupling value may be a current or frequency proportional to the strength of coupling. In some embodiments, the field strength measurement circuit may additionally determine whether the strength of coupling/received power is sufficient to perform an analyte concentration measurement and convey the results thereof to the external sensor reader 101. For example, in some embodiments, the field strength measurement circuit may detect whether the received power is sufficient to produce a certain voltage and/or current. In one non-limiting embodiment, the field strength measurement circuit may detect whether the received power produces a voltage of at least approximately 3V and a current of at least approximately 0.5 mA. However, other embodiments may detect that the received power produces at least a different voltage and/or at least a different current. In one non-limiting embodiment, the field strength measurement circuit may compare the coupling value field strength sufficiency threshold.

In the illustrated embodiment, the clamp/modulator 646 of the I/O circuit 536 acts as the field strength measurement circuit by providing a value (e.g., $I_{couple}$) proportional to the field strength. The field strength value $I_{couple}$ may be provided as an input to the signal MUX 666. When selected, the MUX 666 may output the field strength value $I_{couple}$ to the ADC 664. The ADC 664 may convert the field strength value $I_{couple}$ received from the signal MUX 666 to a digital field strength value signal and supply the digital field strength signal to the measurement controller 532. In this way, the field strength measurement may be made available to the measurement controller 532 for use in initiating an analyte measurement command trigger based on dynamic field alignment. However, in an alternative embodiment, the field strength measurement circuit may instead be an analog oscillator in the sensor 100 that sends a frequency corresponding to the voltage level on a rectifier 640 back to the reader 101.

Figure 12:
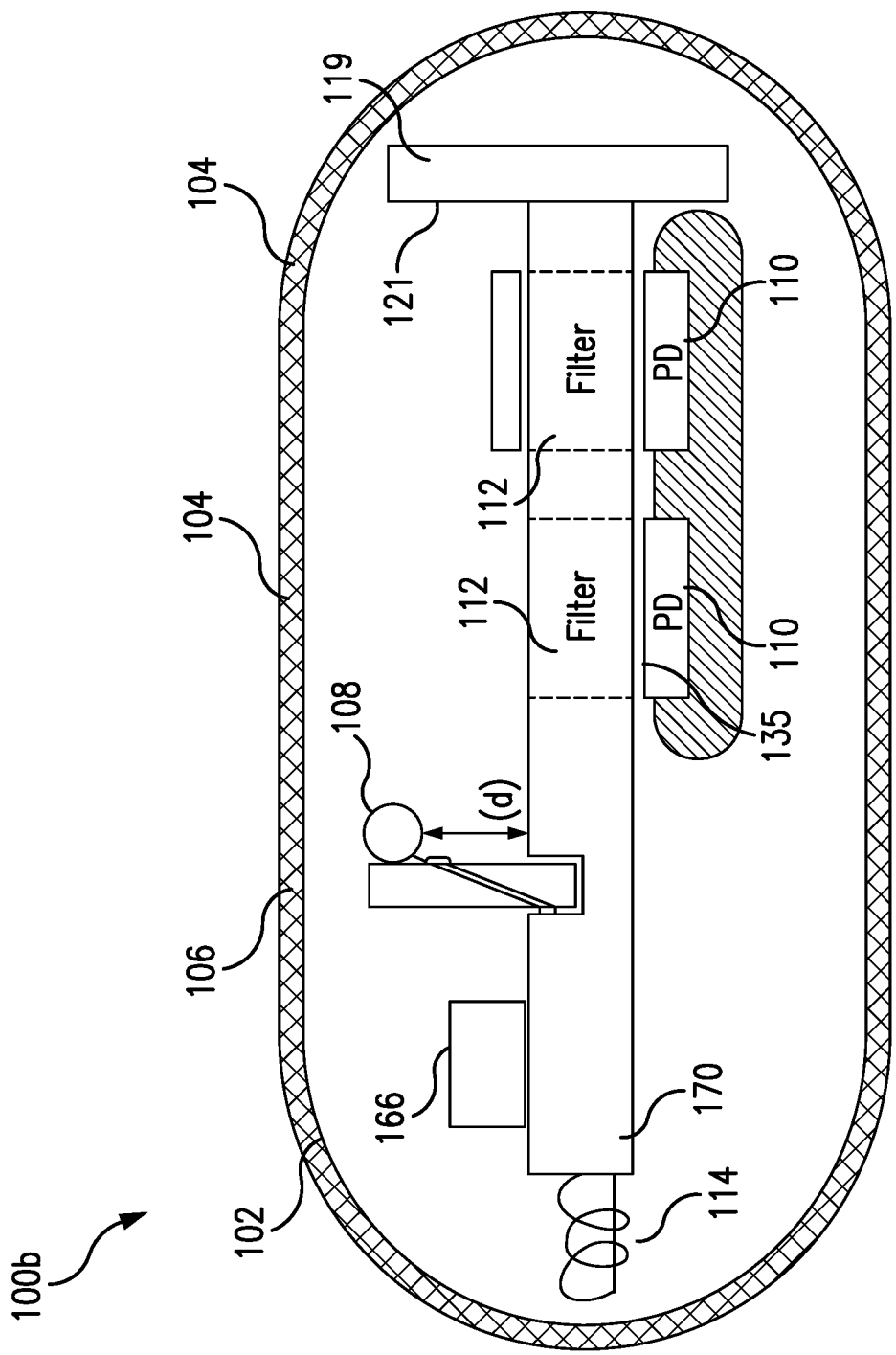
FIG. 12 illustrates an alternative embodiment of a sensor embodying aspects of the present invention.

FIG. 12 is a schematic, section view illustrating sensor 100b, which is an alternative embodiment of the sensor 100. The sensor can be an implanted biosensor, such as the optical based biosensor described in U.S. Pat. No. 7,308,292, the disclosure of which is incorporated by reference herein in its entirety. The sensor 100b may operate based on the fluorescence of fluorescent indicator molecules 104. As shown, sensor 100b may include a sensor housing 102 that may be formed from a suitable, optically transmissive polymer material. Sensor 100b may further include a matrix layer 106 coated on at least part of the exterior surface of the sensor housing 102, with fluorescent indicator molecules 104 distributed throughout the layer 106 (layer 106 can cover all or part of the surface of housing 102). Sensor 100b may include a radiation source 108, e.g., a light emitting diode (LED) or other radiation source, that emits radiation, including radiation over a range of wavelengths which interact with the indicator molecules 104. Sensor 100b also includes a photodetector 110 (e.g., a photodiode, phototransistor, photoresistor or other photosensitive element) which, in the case of a fluorescence-based sensor, is sensitive to fluorescent light emitted by the indicator molecules 104 such that a signal is generated by the photodetector 110 in response thereto that is indicative of the level of fluorescence of the indicator molecules. Two photodetectors 110 are shown in FIG. 12 to illustrate that sensor 100b may have more than one photodetector.

The sensor 100b may be powered by an external power source such as the sensor reader 101 of the present invention. For example, the external power source may generate a magnetic field to induce a current in inductive element 114 (e.g., a copper coil or other inductive element). Circuitry 166 may use inductive element 114 to communicate information to the sensor reader 101. Circuitry 166 may include discrete circuit elements, an integrated circuit (e.g., an application specific integrated circuit (ASIC), and/or other electronic components). The external power source and data reader may be the same device.

In some embodiments, the circuitry 166 of sensor 100b may include a field strength measurement circuit. The field strength measurement circuit may measure the received (i.e., coupled) power (e.g., in mWatts). The field strength measurement circuit of circuitry 166 of sensor 100b may produce a coupling value proportional to the strength of coupling between the inductive element 114 of the sensor 100 and the inductive element of the external reader 101. For example, in non-limiting embodiments, the coupling value may be a current or frequency proportional to the strength of coupling. In some embodiments, the field strength measurement circuit may additionally determine whether the strength of coupling is sufficient for the sensor to perform an analyte concentration measurement and convey the results thereof to the external sensor reader 101. For example, in some non-limiting embodiments, the circuitry 166 of sensor 100b may detect whether the strength of coupling is sufficient to produce a certain voltage and/or current. In one non-limiting embodiment, the field strength measurement circuit may compare the coupling value field strength sufficiency threshold.

Figure 13:
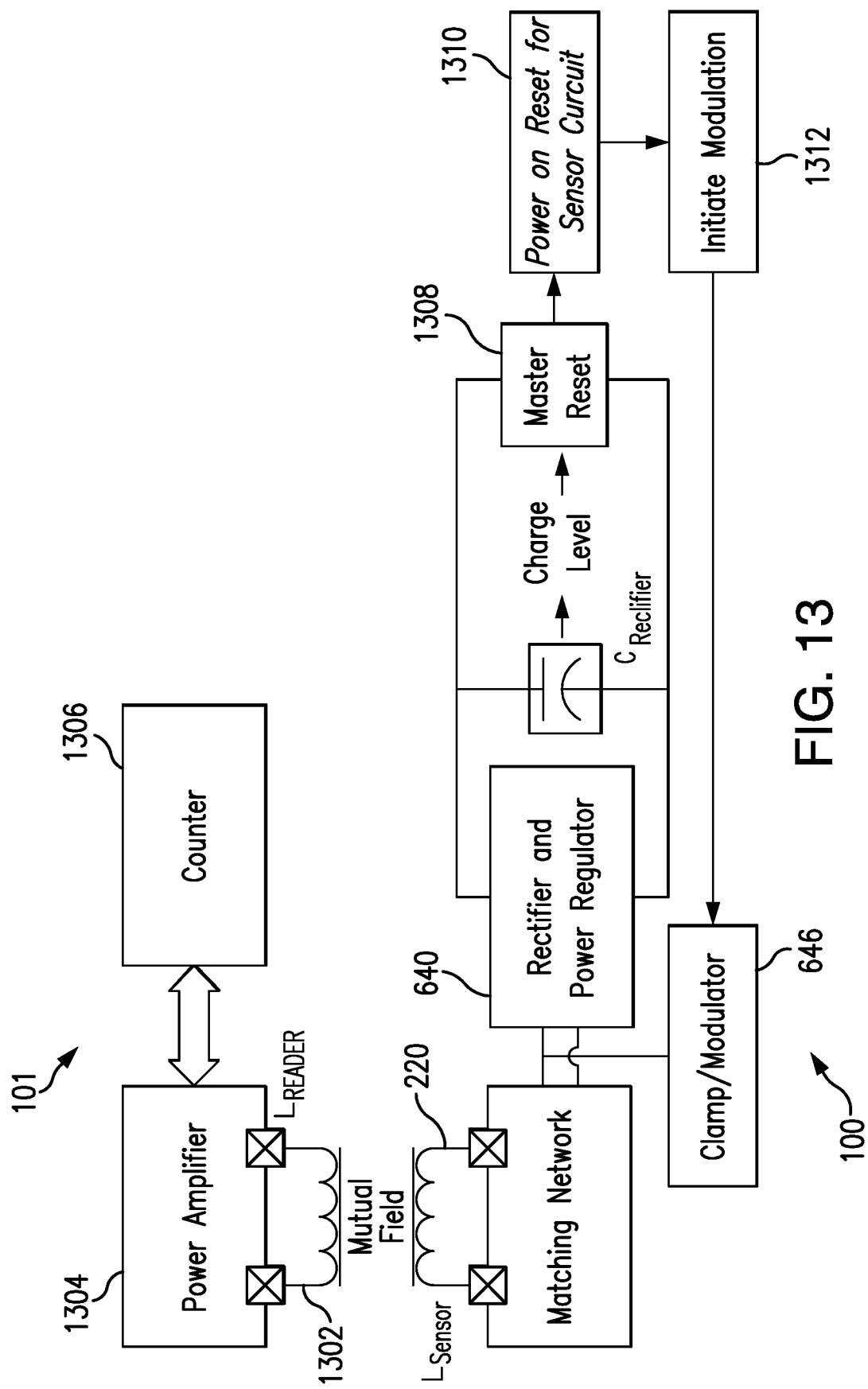
FIG. 13 is a block diagram illustrating functional blocks of the circuitry of an external sensor reader according to an embodiment of the present invention.

In some embodiments, the external sensor reader 101 may include a field strength measurement circuit instead of (or in addition to) having a field strength measurement circuit in the sensor. FIG. 13 illustrates one non-limiting embodiment of an external sensor reader 101 having a field strength measurement circuit. As illustrated in FIG. 13, the external sensor 101 may include an inductive element (e.g., coil) 1302, power amplifier 1304, and a counter 1306, and the sensor 100 may include an inductive element (e.g., coil) 220, rectifier and power regulator 640, clamp/modulator 646, rectifier capacitor $C_{Rectifier}$, master reset block 1308, power on reset block 1310, and initiate modulation block 1312. The counter 1306 may act as a field strength measurement circuit by counting/detecting the amount of time between when the reader 101 begins supplying power (i.e., generates an electrodynamic field) and when the sensor 101 conveys a response communication (e.g., by modulating the electrodynamic field), which is detected/decoded by the external reader 101. The longer it takes for the response communication to be conveyed, the lower the field strength. In this way the counter 1306 may produce a value proportional to the strength of coupling of the inductive element 1302 of the external reader 101 and the inductive element 220 of the sensor 100. In some embodiments, the value may be the count or a current or voltage based on the count.

In the illustrated embodiment, once the reader 101 begins supplying power, a sensor 100 within the electrodynamic field may begin to build charge in the rectifier capacitor $C_{Rectifier}$. Once a certain amount (i.e., the reset charge level) of charge is built up, the master reset block 1308 may reset the sensor 101. Subsequently, the power on reset block 1310 may start up the sensor 100, and the initiate modulate block 1312 may cause a response communication to be conveyed to the reader 101 via the clamp/modulator 646. The strength of the coupling of the inductive element 1302 of the external reader 101 and the inductive element 220 of the sensor 100 determines the amount of time it takes for the rectifier capacitor $C_{Rectifier}$ to charge up to the reset charge level, which determines the length of time it takes for the sensor 101 to convey a response communication to the reader 101. After receiving the response communication, the sensor reader 101 may stop supplying power.

In some embodiments, the reader 101 may use the value proportional to the strength of coupling produced by the counter 1306 to determine whether the strength of coupling is sufficient for the sensor 100 to perform an analyte measurement and to convey the result back to the reader 101.

Figure 14C:
FIGS. 14A-14C illustrate a user using an external sensor reader according to an embodiment of the present invention.
Figure 14A:
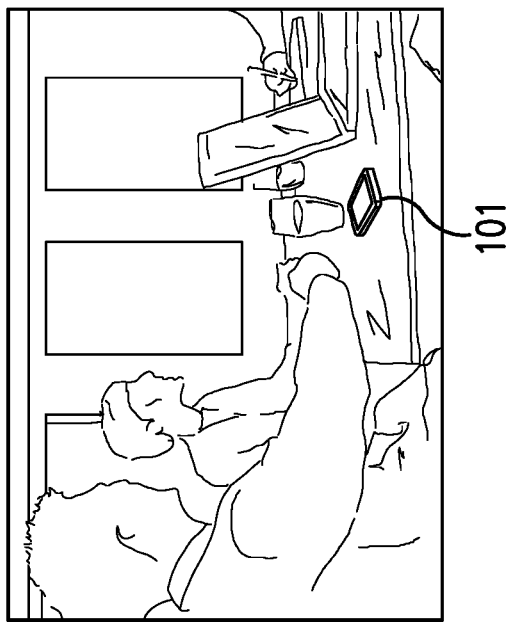
Figure 14B:
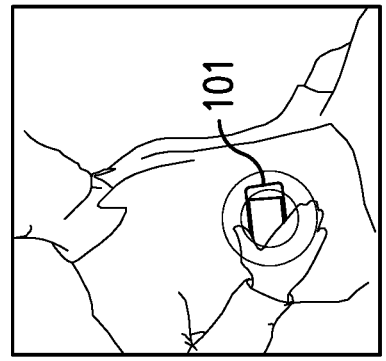

FIGS. 14A-14C illustrate a user using a handheld external sensor reader 101 according to an embodiment of the present invention. The user moves or swipes the sensor reader 101 within a distance, e.g., six inches, of the internal sensor 100, as shown in FIG. 14B. When the sensor reader 101 is moved within the proximity of the sensor 100, and the strength of the electrodynamic field emitted by the inductive element of the sensor reader 101 and received by the inductive element of the sensor 100 is sufficient for the sensor 100 to perform an analyte measurement, the sensor reader 101 may convey an analyte measurement command to the sensor 100, which executes the analyte measurement command and conveys the analyte measurement information to the sensor reader 101. The sensor reader 101 may use the analyte measurement information to display information representing the concentration of the analyte in a medium within a living animal using the user interface 107 of the sensor reader 101.

In one non-limiting embodiment, the measurement controller 532 of the sensor 100 may iteratively compare the value proportional to the coupling strength (e.g., $I_{couple}$) as an indicator of relative field strength, and, when the value meets or exceeds a threshold value such that the reader and sensor are sufficiently coupled within the field to successfully exchange power and data, the measurement controller 532 may issue a command to the reader to take an analyte reading/measurement, which is the motion transient trigger event. Following a successful reading, the system may reset.

Figure 15:
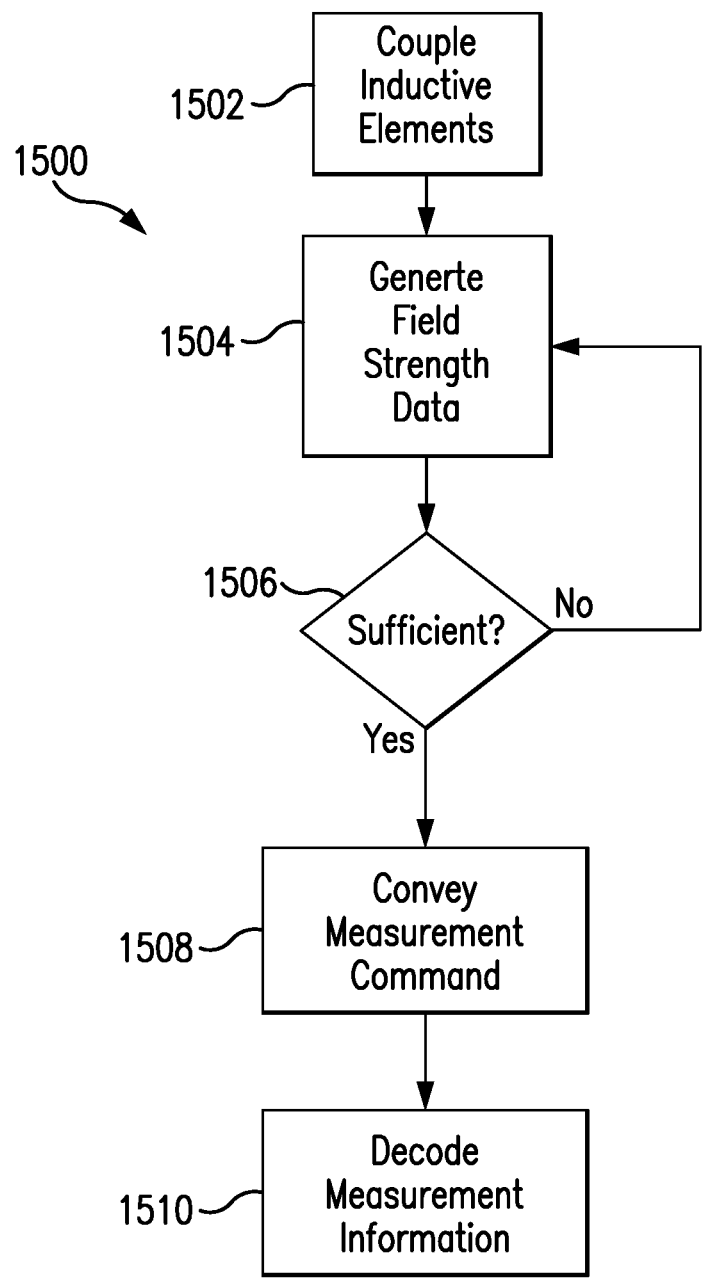
FIG. 15 illustrates an exemplary sensor reader control process that may be performed by the sensor reader in accordance with an embodiment of the present invention.

FIG. 15 illustrates an exemplary sensor reader control process 1500 that may be performed by the sensor reader 101 in accordance with an embodiment of the present invention. The sensor reader control process 1500 may begin with a step 1502 of coupling the inductive element of the external reader 101 and the inductive element 114 of the sensor 100 within an electrodynamic field. In one embodiment, the sensor reader 101 may generate an electrodynamic field via an inductive element of the transceiver 103 of the sensor reader 101 and may, thereby supply power to a sensor 100 coupled within the electrodynamic field. In one non-limiting embodiment, the coupling may comprise moving the sensor 100 and the external reader 101 relative to each other such that the inductive element of the external reader 101 and the inductive element 114 of the sensor 100 are coupled within the electrodynamic field.

In step 1504, the sensor reader 101 may generate field strength data. In some embodiments, the reader 101 may generate the field strength data by producing a coupling value proportional to the strength of the coupling of the inductive element of the external reader 101 and the inductive element 114 of the sensor 100. In one non-limiting embodiment, the coupling value may be produced, for example, by the counter 1306 of the reader 101.

In other embodiments, the sensor 100 may produce the coupling value proportional to the strength of the coupling of the inductive element of the external reader 101 and the inductive element 114 of the sensor 100 and may convey the coupling value to the reader 101 (e.g., by modulating the electrodynamic field in accordance with the coupling value). In these embodiments, the reader 101 may generate the field strength data by decoding coupling value conveyed by the sensor 100. In some embodiments, the sensor 100 may convert (e.g., via ADC 664) the coupling value to a digital coupling value before conveying it to the reader 101. In some embodiments, the sensor 100 may additionally or alternatively convey an indication that the strength of the electrodynamic field received by the sensor 100 is either sufficient or insufficient for the sensor 100 to perform the analyte measurement and convey the analyte measurement results to the reader 101.

In step 1506, the sensor reader 101 may determine whether the strength of the electrodynamic field received by the sensor 100 is sufficient for the sensor 100 to perform an analyte measurement based on the received field strength data. In some non-limiting embodiments, step 1506 may be performed by the processor 105 of the sensor reader 101. In some non-limiting embodiments, the processor 105 of the sensor reader 101 may determine whether the strength of the electrodynamic field received by the sensor 100 is sufficient by comparing the value proportional to the strength of the electrodynamic field to an analyte measurement field strength sufficiency threshold. In other embodiments, the processor 105 of the sensor reader 101 may determine whether the strength of the electrodynamic field received by the sensor 100 is sufficient based on an indication conveyed from the sensor 100 that the strength of the electrodynamic field received by the implanted sensor 100 is either sufficient or insufficient.

If the sensor reader 101 determines that the strength of the electrodynamic field received by the sensor 100 is insufficient for the sensor 100 to perform an analyte concentration measurement and convey the results thereof, the sensor reader control process 1500 may return to step 1504 to receive generate additional field strength data. In some non-limiting embodiments, if the sensor reader 101 determines that the strength of the electrodynamic field received by the sensor 100 is insufficient for the sensor 100 to perform an analyte measurement, the sensor reader 101 may notify the user that the strength of the electrodynamic field received by the sensor 100 is insufficient. For example, the user may be notified by using the user interface 107 of the sensor reader 101. In some non-limiting embodiments, the user interface 107 of the sensor reader 101 may display a signal strength indicator whenever the field strength data is available. In a non-limiting embodiment, the sensor reader 101 may display the value proportional to the strength of the electrodynamic field, in an indication (e.g., a percentage, ratio, or bars) of the strength of the electrodynamic field received by the sensor 100 relative to the received strength that would be sufficient for the sensor 100 to perform an analyte measurement.

If the sensor reader 101 determines that the strength of the electrodynamic field received by the sensor 100 is sufficient for the sensor 100 to perform an analyte measurement, in step 1508, the sensor reader 101 may automatically convey an analyte measurement command and power to the sensor 100. In a non-limiting embodiment, the sensor reader 101 may additionally or alternatively convey other types of commands. In some embodiments, the sensor reader 101 may convey the analyte measurement command by modulating the electrodynamic field using the inductive element of the transceiver 103 of the sensor reader 101.

In step 1510, the sensor reader 101 may decode analyte measurement information conveyed from the sensor 100. The analyte measurement information may be received using the inductive element of the transceiver 103 of the sensor reader 101, and the analyte measurement information may be decoded from modulation of the electrodynamic field. In a non-limiting embodiment, the user interface 107 of the sensor reader 101 may notify the user that the analyte measurement information was successfully received. In some non-limiting embodiments, the processor 105 of the sensor reader 101 may subsequently process the received analyte measurement information to determine a concentration of an analyte, and the user interface 107 may display a value representing the concentration of the analyte so that a user (e.g., the patient, a doctor and/or others) can read the value.

Figure 16:
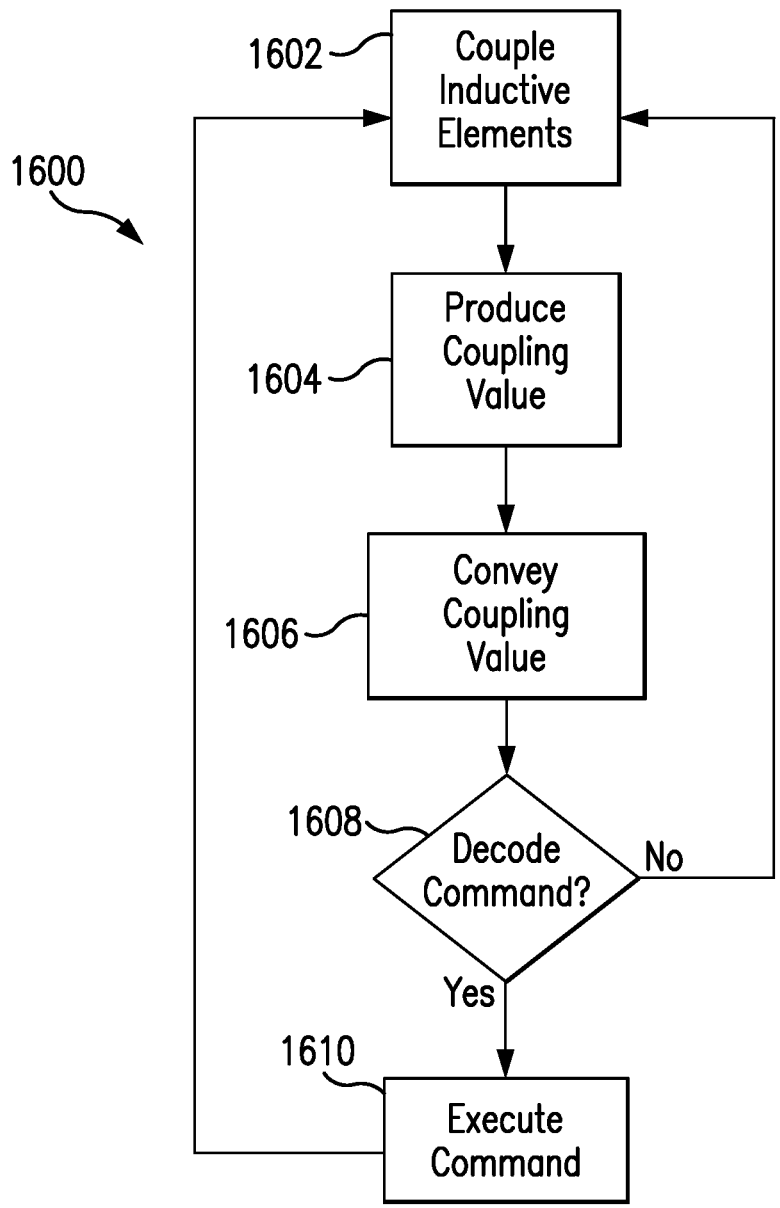
FIG. 16 illustrates an exemplary sensor control process that may be performed by the sensor in accordance with an embodiment of the present invention.

FIG. 16 illustrates an exemplary sensor control process 1600 that may be performed by the sensor 100, which may be, for example, implanted within a living animal (e.g., a living human), in accordance with an embodiment of the present invention. The sensor control process 1600 may begin with a step 1602 of coupling the inductive element of the external reader 101 and the inductive element 114 of the sensor 100 within an electrodynamic field. The sensor 100 may use the electrodynamic field to generate operational power. In one embodiment, the electrodynamic field may induce a current in inductive element 114 of sensor 100, and the input/output (I/O) front end block 536 may convert the induced current into power for operating the sensor 100. In a non-limiting embodiment, rectifier 640 may be used to convert the induced current into operating power for the sensor 100.

In step 1604, circuitry of the sensor 100 may produce a coupling value proportional to the strength of the coupling of the inductive element of the external reader 101 and the inductive element 114 of the sensor 100. In some non-limiting embodiments, the clamp/modulator 646 of the I/O circuit 536 may produce a coupling value (e.g., $I_{couple}$) proportional to the strength of coupling based on the current induced in the inductive element 114 by the electrodynamic field. In one non-limiting embodiment, the coupling value $I_{couple}$ proportional to the field strength may be converted (e.g., by ADC 664) to a digital coupling value proportional to the received field strength.

In some non-limiting embodiments, the coupling value may be used by the sensor 100 to determine whether the strength of the electrodynamic field received by the sensor 100 is sufficient for the sensor 100 to perform an analyte measurement. For instance, in one non-limiting embodiment, the measurement controller 532 may compare the coupling value to an analyte measurement field strength sufficiency threshold and produce an indication that the strength of the electrodynamic field received by the sensor is either sufficient or insufficient for the implanted sensor to perform the analyte measurement.

In step 1606, the sensor 100 may convey the analog or digital coupling value to the sensor reader 101 (e.g., by modulating the electrodynamic field). In one embodiment, the measurement controller 532 may output the digital coupling value to the data and control bus 654. The data and control bus 654 may transfer the digital coupling value to the command decoder/data encoder 652, which may encode the digital coupling value. The data serializer 656 may serialize the encoded digital coupling value. The encoder 658 may encode the serialized digital coupling value. The clamp/modulator 646 may modulate the current flowing through the inductive element 114 (e.g., coil 220) as a function of the encoded digital coupling value. In this way, the encoded digital coupling value may be conveyed by the inductive element 114 as a modulated electromagnetic wave. In some embodiments, the encoded digital coupling value conveyed by the sensor 100 may be decoded by the sensor reader 101.

In step 1608, the sensor 100 may determine whether a command has been decoded (e.g., from modulation of the electrodynamic field). In one non-limiting embodiment, the I/O front end block 536 and I/O controller 538 may convert the induced current into power for operating the sensor 100 and extract and decode any received commands from the induced current. In a non-limiting embodiment, rectifier 640 may be used to convert the induced current into operating power for the sensor 100, data extractor 642 may extract data from the current induced in inductive element 114, decoder/serializer 650 may decode and serialize the extracted data, and command decoder/data encoder 652 may decode one or more commands from the decoded and serialized extracted data. Any decoded commands may then be sent to measurement controller 532 via the data and control bus 654. In some embodiments, the one or more commands and power received by the sensor 100 may be transmitted by the transceiver 103 of sensor reader 101.

If a command has not been decoded, the sensor control process 1600 may return to step 1602. If a command has been decoded, in step 1610, the sensor 100 may execute the decoded command. For example, in one embodiment, the sensor 100 may execute the decoded command under control of the measurement controller 532. Example command execution processes that may be performed by the sensor 100 in step 1610 to execute the decoded commands are described below with reference to FIGS. 17-20.

Examples of commands that may be received and executed by the sensor 100 may include analyte measurement commands, get result commands and/or get traceability information commands. Examples of analyte measurement commands may include measure sequence commands (i.e., commands to perform a sequence of measurements, and after finishing the sequence, transmitting the resulting measurement information), measure and save commands (i.e., commands to perform a sequence of measurements and, after finishing the sequence, saving the resulting measurement information without transmitting the resulting measurement information) and/or single measurement commands (i.e., commands to perform a single measurement). The single measurement commands may be commands to save and/or transmit the measurement information resulting from the single measurement. The analyte measurement commands may or may not include setup parameters (i.e., calibration information).

Measurement commands that do not have setup parameters may, for example, be executed using stored setup parameters (e.g., in nonvolatile storage medium 660). Other analyte measurement commands, such as measurement commands to both save and transmit the resulting measurement information, are possible. The commands that may be received and executed by the sensor 100 may also include commands to update the stored the setup parameters. The examples of commands described above are not exhaustive of all commands that may be received and executed by the sensor 100, which may be capable of receiving and executing one or more of the commands listed above and/or one or more other commands.

Figure 17:
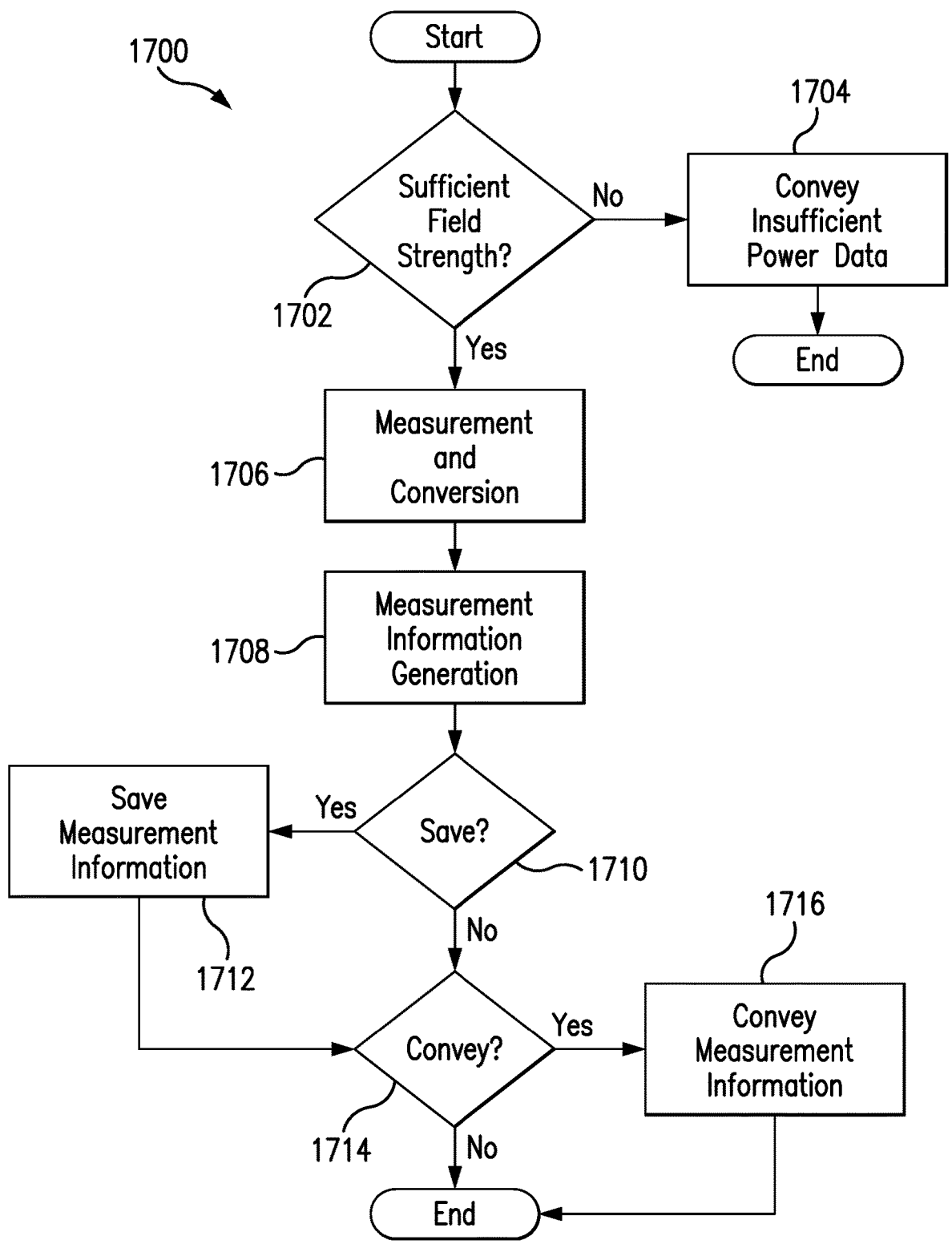
FIG. 17 illustrates a measurement command execution process that may be performed by the sensor to execute a measurement command received by the sensor in accordance with an embodiment of the present invention.

FIG. 17 illustrates an analyte measurement command execution process 1700 that may be performed in step 1610 of the sensor control process 1600 by the sensor 100 to execute an analyte measurement command received by the sensor 100 in accordance with an embodiment of the present invention. In a non-limiting embodiment, the analyte measurement command execution process 1700 may begin with a step 1702 of determining whether the field strength is sufficient to execute the received measurement command. In other words, in step 1702, the sensor 100 may determine whether the electromagnetic field or wave that may induce a current in inductive element 114 is strong enough to generate sufficient operating power for execution of the decoded measurement command, which, as described below, may include using light source 108 to irradiate indicator molecules 104. In one embodiment, step 1702 may be performed by a field strength measurement circuit, which may be part of the measurement controller 532 or may be a separate component of the circuitry 776 on the silicon substrate 116.

In some embodiments, if the sensor 100 determines in step 1702 that the field strength is insufficient to execute the received measurement command, the analyte measurement command execution process 1700 may proceed to a step 1704 in which the sensor 100 may convey (e.g., by way of the input/output (I/O) front end block 536, I/O controller 538, and inductive element 114) data indicating that that the wirelessly received power is insufficient to execute the received analyte measurement command. In some embodiments, the insufficient power data may merely indicate that the power is insufficient, but in other embodiments, the insufficient power data may indicate the percentage of the power needed to execute the received measurement command that is currently being received.

In one embodiment, upon detection that the received power is insufficient, the measurement controller 532 may output insufficient power data to the data and control bus 654. The data and control bus 654 may transfer the insufficient power data to the command decoder/data encoder 652, which may encode the insufficient power data. The data serializer 656 may serialize the encoded insufficient power data. The encoder 658 may encode the serialized insufficient power data. The clamp/modulator 646 may modulate the current flowing through the inductive element 114 (e.g., coil 220) as a function of the encoded insufficient power data. In this way, the encoded insufficient power data may be conveyed by the inductive element 114 as a modulated electromagnetic wave. In some embodiments, the encoded insufficient power data conveyed by the sensor 100 may be received by the sensor reader 101, which may display a message on user interface 107 a message indicating that the power received by the sensor 100 is insufficient and/or the extent to which the received power is insufficient.

In some alternative embodiments, steps 1702 and 1704 are not performed, and the sensor 100 assumes that, if an analyte measurement command has been decoded, the field strength is sufficient.

In step 1706 in which a measurement and conversion process may be performed. The measurement and conversion process may, for example, be performed by the analog interface 534 under control of the measurement controller 532. In one embodiment, the measurement and conversion sequence may include generating one or more analog measurements (e.g., using one or more of temperature transducer 670, light source 108, first photodetector 224, second photodetector 226 and/or comparator 668) and converting the one or more analog measurements to one or more digital measurements (e.g., using ADC 664). One example of the measurement conversion process that may be performed in step 1706 is described in further detail below with reference to FIG. 18.

At step 1708, the sensor 100 may generate measurement information in accordance with the one or more digital measurements produced during the measurement and conversion sequence performed in step 1706. Depending on the one or more digital measurements produced in step 1706, the measurement information may be indicative of the presence and/or concentration of an analyte in a medium in which the sensor 100 is implanted. In one embodiment, in step 1706, the measurement controller 532 may receive the one or more digital measurements and generate the measurement information.

At step 1710, the sensor 100 may determine whether the analyte measurement information generated in step 1708 should be saved. In some embodiments, the measurement controller 532 may determine whether the analyte measurement information should be saved. In one embodiment, the measurement controller 532 may determine whether measurement information should be saved based on the received measurement command. For example, if the analyte measurement command is a measure and save command or other measurement command that includes saving the resulting measurement information, the measurement controller 532 may determine that the analyte measurement information generated in step 1708 should be saved. Otherwise, if the analyte measurement command is a measure sequence command or other analyte measurement command that does not include saving the resulting measurement information, the measurement controller 532 may determine that the analyte measurement information generated in step 1708 should not be saved.

In some embodiments, if the sensor 100 determines in step 1710 that the analyte measurement information generated in step 1708 should be saved, the analyte measurement command execution process 1700 may proceed to a step 1712 in which the sensor 100 may save the measurement information. In one embodiment, after determining that the analyte measurement information generated in step 1708 should be saved, the measurement controller 532 may output the analyte measurement information to the data and control bus 654, which may transfer the analyte measurement information to the nonvolatile storage medium 660. The nonvolatile storage medium 660 may save the received analyte measurement information. In some embodiments, the measurement controller 532 may output, along with the analyte measurement information, an address at which the measurement information is to be saved in the nonvolatile storage medium 660. In some embodiments, the nonvolatile storage medium 660 may be configured as a first-in-first-out (FIFO) or last-in-first-out (LIFO) memory.

In some embodiments, if the sensor 100 determines in step 1710 that the analyte measurement information generated in step 1708 should not be saved, or after saving the analyte measurement information in step 1712, the analyte measurement command execution process 1700 may proceed to a step 1714 in which the sensor 100 may determine whether the analyte measurement information generated in step 1708 should be conveyed. In some embodiments, the measurement controller 532 may determine whether the measurement information should be transmitted. In one embodiment, the measurement controller 532 may determine whether the measurement information should be conveyed based on the received measurement command. For example, if the analyte measurement command is a measure sequence command or other measurement command that includes transmitting the resulting measurement information, the measurement controller 532 may determine that the measurement information generated in step 1708 should be conveyed. Otherwise, if the analyte measurement command is a measure and save command or other measurement command that does not include conveying the resulting analyte measurement information, the measurement controller 532 may determine that the analyte measurement information generated in step 1708 should not be conveyed.

In some embodiments, if the sensor 100 determines in step 1714 that the analyte measurement information generated in step 1708 should be conveyed, the analyte measurement command execution process 1700 may proceed to a step 1716 in which the sensor 100 may convey the analyte measurement information. In one embodiment, after determining that the measurement information generated in step 1708 should be convey, the measurement controller 532 may output the measurement information to the data and control bus 654. The data and control bus 654 may transfer the analyte measurement information to the command decoder/data encoder 652, which may encode the measurement information. The data serializer 656 may serialize the encoded measurement information. The encoder 658 may encode the serialized measurement information. The clamp/modulator 646 may modulate the current flowing through the inductive element 114 (e.g., coil 220) as a function of the encoded measurement information. In this way, the encoded measurement information may be transmitted wirelessly by the inductive element 114 as a modulated electromagnetic wave. In some embodiments, the encoded measurement information wirelessly transmitted by the sensor 100 may be received by the sensor reader 101, which may display a value representing the concentration of the analyte so that a user (e.g., the patient, a doctor and/or others) can read the value.

In some embodiments, after the sensor 100 (a) conveyed insufficient power data in step 1704, (b) determined in step 1714 that the measurement information generated in step 1708 should not be conveyed or (c) conveyed measurement information in step 1716, the analyte measurement command execution process 1700 that may be performed in step 1610 of the sensor control process 1600 by the sensor 100 to execute an analyte measurement command received by the sensor 100 may be completed, and, at this time, the sensor control process 1600 may return to step 1602.

In some alternative embodiments, steps 1710, 1712, and 1714 are not performed, and the sensor 100 proceeds directly to step 1710 to convey the analyte measurement information after completing the measurement information generation in step 1708.

Figure 18:
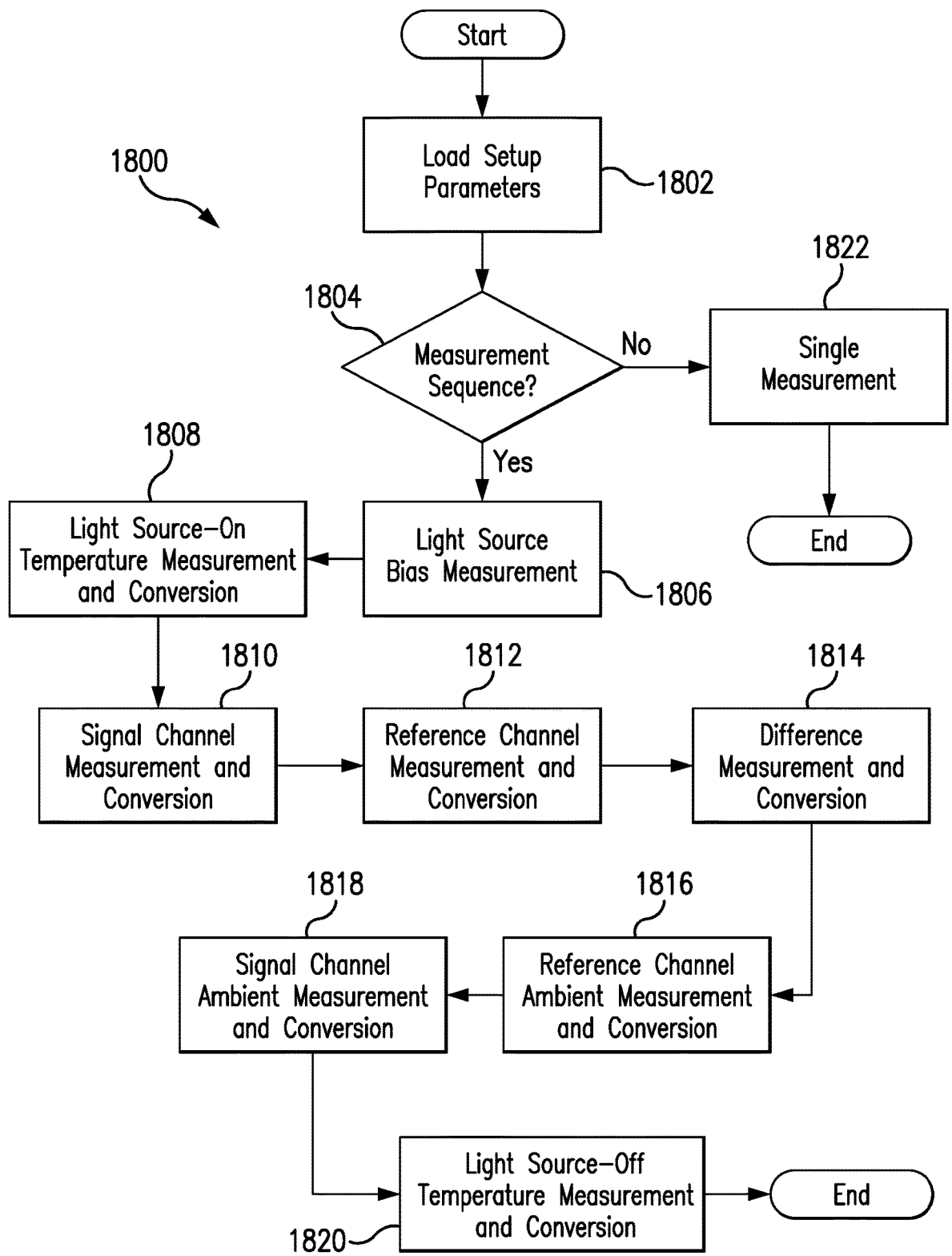
FIG. 18 illustrates a measurement and conversion process that may be performed in a step of the measurement command execution process, in accordance with an embodiment of the present invention.

FIG. 18 illustrates a measurement and conversion process 1800, which is an example of the measurement and conversion process that may be performed in step 1706 of the analyte measurement command execution process 1700, in accordance with an embodiment of the present invention.

At step 1802, the sensor 100 may load setup parameters (i.e., calibration information) for performing one or more measurements in accordance with the received measurement command. For example, in one embodiment, the measurement controller 532 may load one or more setup parameters by setting up one or more components (e.g., light source 108, first photodetector 224, second photodetector 226, comparator 668 and/or temperature transducer 534) of the analog interface 534 with the setup parameters. In some embodiments, the nonvolatile storage medium 660 may store saved setup parameters. Further, as noted above, in some embodiments, the measurement commands may or may not include setup parameters. In a non-limiting embodiment, if the measurement command includes one or more setup parameters, the measurement controller 532 may setup one or more components of the analog interface 534 with the setup parameters with the one or more setup parameters included in the measurement command. However, if the measurement command does not include one or more setup parameters, the measurement controller 532 may obtain saved setup parameters stored in the nonvolatile storage medium 660 and setup one or more components of the analog interface 534 with the saved setup parameters obtained from the nonvolatile storage medium 660.

At step 1804, the sensor 100 may determine whether to execute a single measurement or a measurement sequence.

In some embodiments, the measurement controller 532 may make the single measurement vs. measurement sequence determination by referring to the received measurement command (i.e., is the measurement command to execute a single measurement or to execute a measurement sequence?). For example, in some embodiments, if the measurement command is a measure sequence command, a measure and save command or other command for a measurement sequence, the measurement controller 532 may determine that a measurement sequence should be executed. However, if the measurement command is a single measurement command, the measurement controller 532 may determine that a single measurement should be executed.

In some embodiments, if the sensor 100 determines in step 1804 that a measurement sequence should be performed, the sensor 100 may perform measurement and conversion sequence steps 1806-1820 of measurement and conversion process 1800. However, in other embodiments, the sensor 100 may perform a portion of measurement and conversion sequence steps 1806-1820 and/or additional measurement and conversion sequence steps.

At step 1806, the sensor 100 may perform a light source bias measurement and conversion. For example, in some embodiments, while the light source 108 is on (i.e., while the light source 108, under the control of the measurement controller 532, is emitting excitation light and irradiating indicator molecules 104), the analog interface 534 may generate an analog light source bias measurement signal. In one embodiment, the ADC 664 may convert the analog light source bias measurement signal to a digital light source bias measurement signal. The measurement controller 532 may receive the digital light source bias measurement signal and generate (e.g., in step 1708 of the measurement command execution process 1700) the measurement information in accordance with the received digital light source bias measurement signal. In a non-limiting embodiment, the analog interface 534 may generate the analog light source bias measurement signal by sampling the voltage and the current in the output of the current source that feeds the light source 108.

At step 1808, the sensor 100 may perform a light source-on temperature measurement and conversion. For example, in some embodiments, while the light source 108 is on (i.e., while the light source 108, under the control of the measurement controller 532, is emitting excitation light and irradiating indicator molecules 104), the analog interface 534 may generate a first analog temperature measurement signal indicative of a temperature of the sensor 100. In one embodiment, the temperature transducer 670 may generate the first analog temperature measurement signal while the light source 108 is on. The ADC 664 may convert the first analog temperature measurement signal to a first digital temperature measurement signal. The measurement controller 532 may receive the first digital temperature measurement signal and generate (e.g., in step 1708 of the measurement command execution process 1700) the measurement information in accordance with the received first digital temperature measurement signal.

At step 1810, the sensor 100 may perform a first photodetector measurement and conversion. For example, in some embodiments, while the light source 108 is on (i.e., while the light source 108, under the control of the measurement controller 532, is emitting excitation light and irradiating indicator molecules 104), the first photodetector 224 may generate a first analog light measurement signal indicative of the amount of light received by the first photodetector 224 and output the first analog light measurement signal to the signal MUX 666. The signal MUX 666 may select the first analog light measurement signal and, the ADC 664 may convert the first analog light measurement signal to a first digital light measurement signal. The measurement controller 532 may receive the first digital light measurement signal and generate (e.g., in step 1708 of the measurement command execution process 1700) the measurement information in accordance with the received first digital light measurement signal.

In a non-limiting embodiment, first photodetector 224 may be a part of a signal channel, the light received by the first photodetector 224 may be emitted by indicator molecules 104 distributed throughout the indicator membrane 106', and the first analog light measurement signal may be an indicator measurement.

At step 1812, the sensor 100 may perform a second photodetector measurement and conversion. For example, in some embodiments, while the light source 108 is on (i.e., while the light source 108, under the control of the measurement controller 532 is emitting excitation light and irradiating indicator molecules 104), the second photodetector 226 may generate a second analog light measurement signal indicative of the amount of light received by the second photodetector 226 and output the second analog light measurement signal to the signal MUX 666. The signal MUX 666 may select the second analog light measurement signal and, the ADC 664 may convert the second analog light measurement signal to a second digital light measurement signal. The measurement controller 532 may receive the second digital light measurement signal and generate (e.g., in step 1708 of the measurement command execution process 1700) the measurement information in accordance with the received second digital light measurement signal.

In a non-limiting embodiment, second photodetector 226 may be a part of a reference channel, the light received by the second photodetector 226 may be emitted by indicator molecules 104 distributed throughout the reference membrane 106", and the second analog light measurement signal may be a reference measurement.

At step 1814, the sensor 100 may perform a difference measurement and conversion. For example, in some embodiments, while the light source 108 is on (i.e., while the light source 108, under the control of the measurement controller 532, is emitting excitation light and irradiating indicator molecules 104), (i) the first photodetector 224 may generate a first analog light measurement signal indicative of the amount of light received by the first photodetector 224, and (ii) the second photodetector 226 may generate a second analog light measurement signal indicative of the amount of light received by the second photodetector 226. The comparator 668 may receive the first and second analog light measurement signals and generate an analog light difference measurement signal indicative of a difference between the first and second analog light measurement signals. The comparator 668 may output the analog light difference measurement signal to the signal MUX 666. The signal MUX 666 may select the analog light difference measurement signal and, the ADC 664 may convert the analog light difference measurement signal to a digital light difference measurement signal. The measurement controller 532 may receive the digital light difference measurement signal and generate (e.g., in step 1708 of the measurement command execution process 1700) the measurement information in accordance with the received digital light difference measurement signal.

In a non-limiting embodiment, first photodetector 224 may be a part of a signal channel, second photodetector 226 may be a part of a reference channel, and the analog light difference measurement signal may be indicative of the difference in light emitted by (a) indicator molecules 104 distributed throughout indicator membrane 106' and affected by the concentration of an analyte in the medium in which sensor 100 is implanted, and (b) indicator molecules 104 distributed throughout reference membrane 106" and unaffected by the concentration of the analyte in the medium in which sensor 100 is implanted.

At step 1816, the sensor 100 may perform a second photodetector ambient measurement and conversion. For example, in some embodiments, while the light source 108 is off (i.e., while the light source 108, under the control of the measurement controller 532 is not emitting light), the second photodetector 226 may generate a second analog ambient light measurement signal indicative of the amount of light received by the second photodetector 226 and output the second analog ambient light measurement signal to the signal MUX 666. The signal MUX 666 may select the second analog ambient light measurement signal and, the ADC 664 may convert the second analog ambient light measurement signal to a second digital ambient light measurement signal. The measurement controller 532 may receive the second digital ambient light measurement signal and generate (e.g., in step 1708 of the measurement command execution process 1700) the measurement information in accordance with the received second digital ambient light measurement signal.

In a non-limiting embodiment, second photodetector 226 may be a part of a reference channel, the light received by the second photodetector 226 may be emitted by indicator molecules 104 distributed throughout the reference membrane 106", and the second analog ambient light measurement signal may be an ambient reference measurement.

At step 1818, the sensor 100 may perform a first photodetector ambient measurement and conversion. For example, in some embodiments, while the light source 108 is off (i.e., while the light source 108, under the control of the measurement controller 532, is not emitting light), the first photodetector 224 may generate a first analog ambient light measurement signal indicative of the amount of light received by the first photodetector 224 and output the first analog ambient light measurement signal to the signal MUX 666. The signal MUX 666 may select the first analog ambient light measurement signal and, the ADC 664 may convert the first analog ambient light measurement signal to a first digital ambient light measurement signal. The measurement controller 532 may receive the first digital ambient light measurement signal and generate (e.g., in step 1708 of the measurement command execution process 1700) the measurement information in accordance with the received first digital ambient light measurement signal.

In a non-limiting embodiment, first photodetector 224 may be a part of a signal channel, the light received by the first photodetector 224 may be emitted by indicator molecules 104 distributed throughout the indicator membrane 106', and the first analog ambient light measurement signal may be an ambient indicator measurement.

At step 1820, the sensor 100 may perform a light source-off temperature measurement and conversion. For example, in some embodiments, while the light source 108 is off (i.e., while the light source 108, under the control of the measurement controller 532, is not emitting light), the analog interface 534 may generate a second analog temperature measurement signal indicative of a temperature of the sensor 100. In one embodiment, the temperature transducer 670 may generate the second analog temperature measurement signal while the light source 108 is off. The ADC 664 may convert the second analog temperature measurement signal to a second digital temperature measurement signal. The measurement controller 532 may receive the second digital temperature measurement signal and generate (e.g., in step 1708 of the measurement command execution process 1700) the measurement information in accordance with the received second digital temperature measurement signal.

Accordingly, in an embodiment in which sequence steps 1806-1820 of measurement and conversion process 1800 are performed, the measurement controller 532 may generate measurement information in accordance with (i) the first digital temperature measurement signal, (ii) the first digital light measurement signal, (iii) the second digital light measurement signal, (iv) the digital light difference measurement signal, (v) the second digital temperature measurement signal, (vi) the first digital ambient light measurement signal and (vii) the second digital ambient light measurement signal. In a non-limiting embodiment, the calculation of the concentration of the analyte performed by the measurement controller 532 of sensor 100 and/or sensor reader 101 may include subtracting the digital ambient light signals from the corresponding digital light measurement signals. The calculation of the concentration of the analyte may also include error detection. In some embodiments, the measurement controller 532 may incorporate methods for attenuating the effects of ambient light, such as, for example, those described in U.S. Pat. No. 7,227,156, which is incorporated herein by reference in its entirety. In some embodiments, the measurement controller 532 may generate measurement information that merely comprises the digital measurement signals received from the analog interface 534. However, in other embodiments, the measurement controller 532 may process the digital signals received from the analog interface 534 and determine (i.e., calculate and/or estimate) the concentration of an analyte in the medium in which the sensor 100 is implanted, and the measurement information may, additionally or alternatively, include the determined concentration.

In some embodiments, if the sensor 100 determines in step 1804 that a measurement sequence should be performed, the measurement and conversion process 1800 may proceed to a step 1822 in which a single measurement and conversion is performed. In some embodiments, based on the measurement command received, the single measurement and conversion performed in step 1822 may be any one of the measurements and conversions performed in steps 1806-1820. Accordingly, in an example where step 1822 of the measurement and conversion process 1800 is performed, the measurement controller 532 may receive only one digital measurement signal, and the measurement information generated by the measurement controller 532 (e.g., in step 1708 of the measurement command execution process 1700) may, in one embodiment, simply be the one digital measurement signal received by the measurement controller.

In some embodiments, light source 108 may be turned on before execution of step 1806 and not turned off until after execution of step 1814. However, this is not required. For example, in other embodiments, the light source 108 may be turned on during measurement portions of steps 1806-1814 and turned off during the conversion portions of steps 1806-1814.

Furthermore, although FIG. 18 illustrates one possible sequence of the measurement and conversion process 1800, it is not necessary that steps 1806-1820 of the measurement and conversion process 1800 be performed in any particular sequence. For example, in one alternative embodiment, light measurement and conversion steps 1806-1814 may be performed in a different order (e.g., 1808, 1812, 1814, 1810, 1806), and/or ambient light measurement and conversion steps 1816-1820 may be performed in a different order (e.g., 1818, 1820, 1816). In some embodiments, the light source on temperature measurement may be used to provide an error flag in each individual measurement (e.g., by using a comparator to comparing the light source on temperature measurement to threshold value). In another alternative embodiment, ambient light measurement and conversion steps 1816-1820 may be performed before light measurement and conversion steps 1806-1814. In still another alternative embodiment, steps 1806-1820 of the measurement and conversion process 1800 may be performed in a sequence in which all of the steps of one of light measurement and conversion steps 1806-1814 and ambient light measurement and conversion steps 1816-1820 are completed before one or more steps of the other are executed (e.g., in one embodiment, steps 1806-1820 may be performed in the sequence 1806, 1808, 1810, 1818, 1816, 1812, 1814, 1820).

Figure 21A:
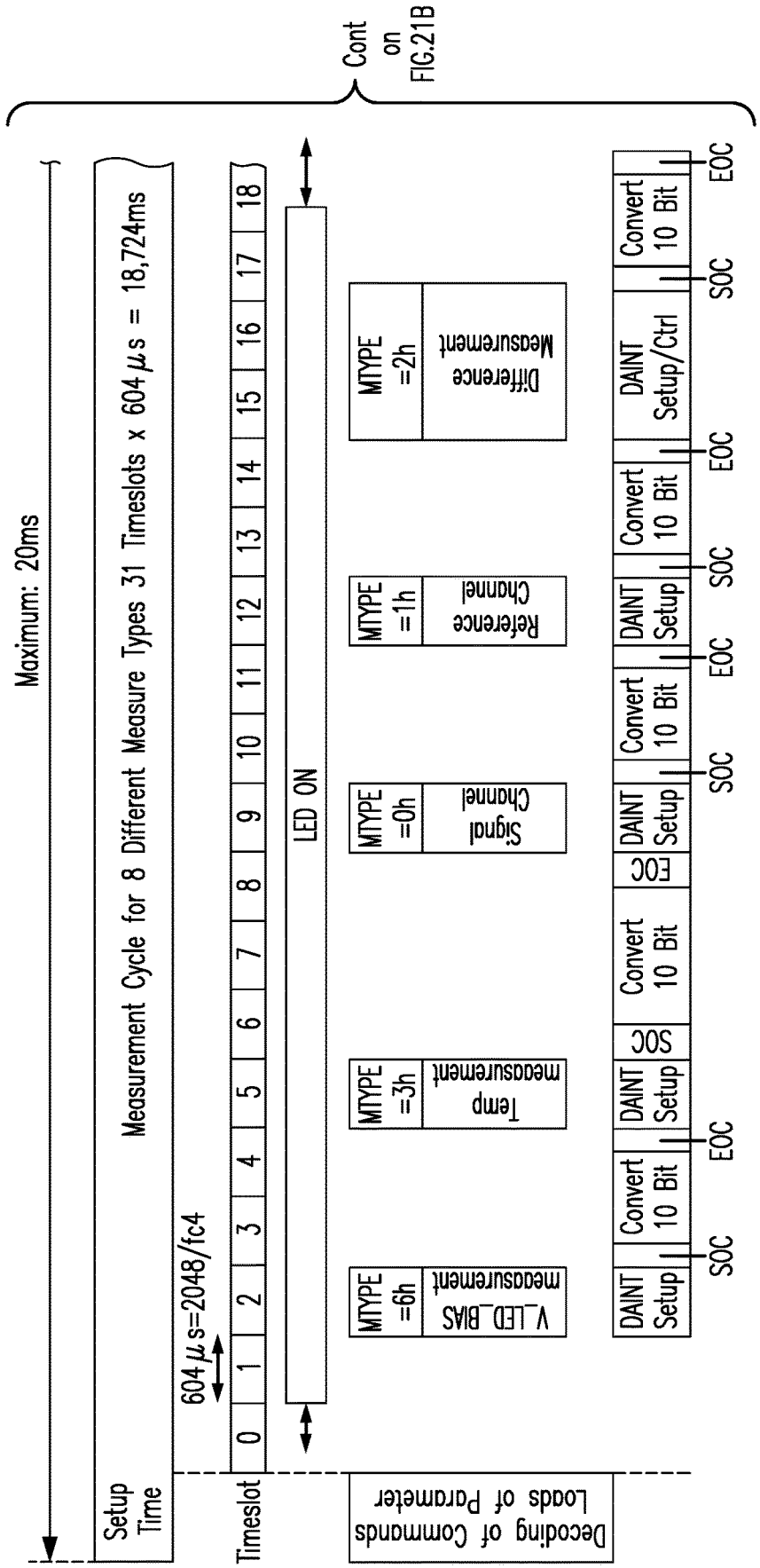
FIGS. 21A and 21B illustrate the timing of an exemplary embodiment of a measurement and conversion process in accordance with an embodiment of the present invention.
Figure 21B:
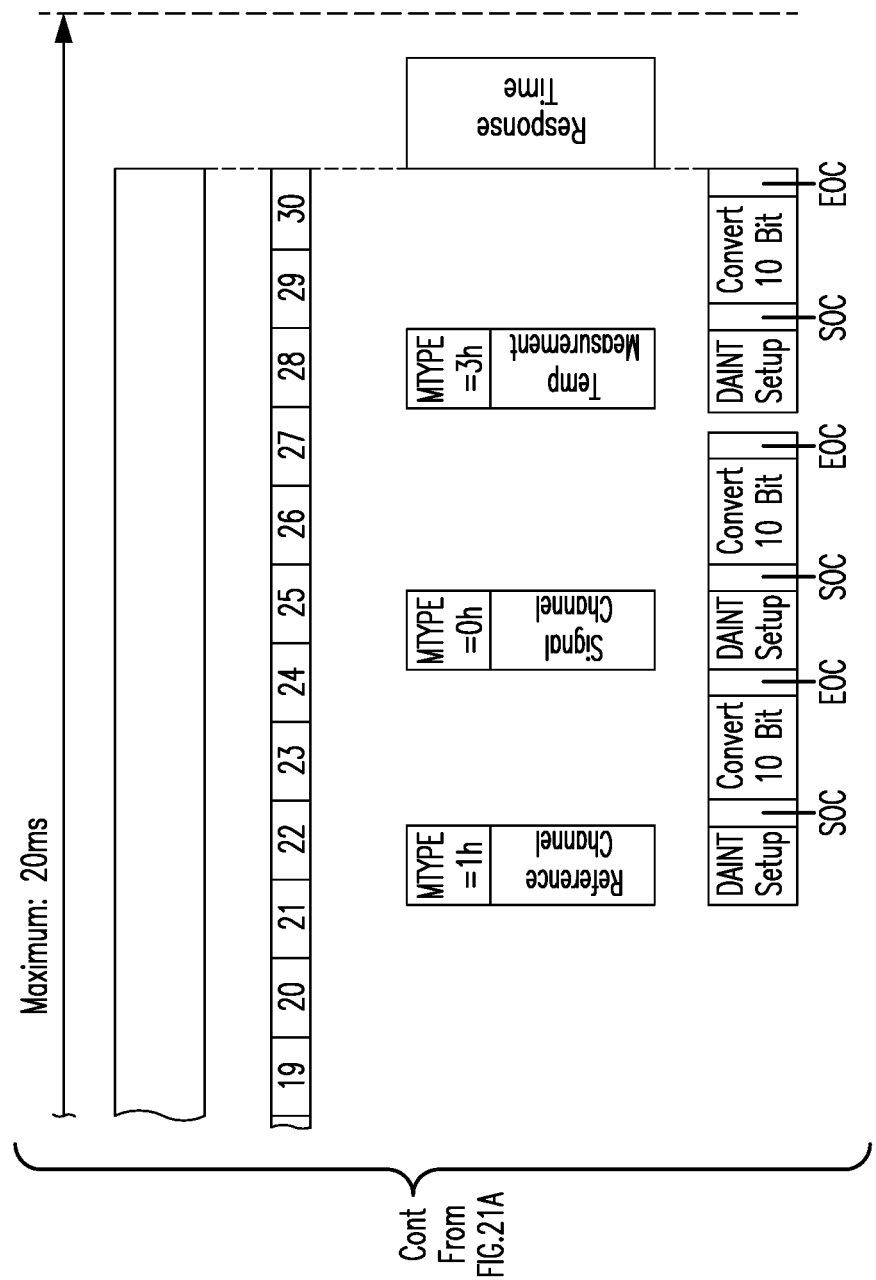

FIGS. 21A and 21B illustrates the timing of an exemplary embodiment of the measurement and conversion process 1800 described with reference to FIG. 18.

Figure 19:
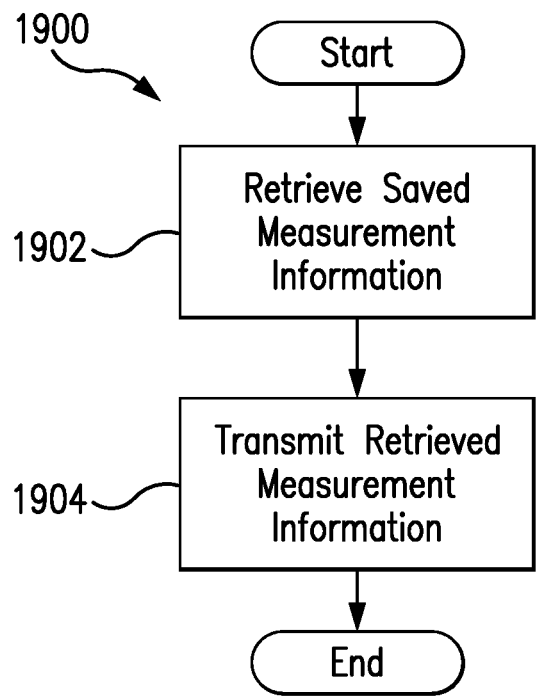
FIG. 19 illustrates a get result command execution process that may be performed by the sensor to execute a get result command received by the sensor in accordance with an embodiment of the present invention.

FIG. 19 illustrates a get result command execution process 1900 that may be performed in step 1610 of the sensor control process 1600 by the sensor 100 to execute a get result command received by the sensor 100 in accordance with an embodiment of the present invention. The measurement command execution process 1900 may begin with a step 1902 of retrieving saved measurement information. For example, retrieved measurement information may be saved during step 1712 of the analyte measurement command execution process 1700 shown in FIG. 17. In some embodiments, measurement information is saved in the nonvolatile storage medium 660. In response to a request from the measurement controller 532, the nonvolatile storage medium 660 may output saved measurement information to the data and control bus 654. In some embodiments, the data and control bus 654 may transfer the retrieved measurement information to the measurement controller 532. However, in alternative embodiments, the data and control bus 654 may transfer the retrieved measurement information to the command decoder/data encoder 652 without first transferring the retrieved measurement information to the measurement controller 532.

In some embodiments, the nonvolatile storage medium 660 may output to the data and control bus 654 the measurement information most recently saved to the nonvolatile storage medium 660. In some alternative embodiments, the nonvolatile storage medium 660 may output to the data and control bus 654 the oldest measurement information most saved to the nonvolatile storage medium 660. In other alternative embodiments, the nonvolatile storage medium 660 may output to the data and control bus 654 the measurement information specifically requested by the measurement controller 532 (e.g., by an address sent to the nonvolatile storage medium 660 with a read request).

After the saved measurement information is retrieved, the get result command execution process 1900 may proceed to a step 1904 in which the sensor 100 may convey the retrieved measurement information. In one embodiment, the measurement controller 532 may output the retrieved measurement information to the data and control bus 654. The data and control bus 654 may transfer the measurement information to the command decoder/data encoder 652, which may encode the retrieved measurement information. The data serializer 656 may serialize the encoded retrieved measurement information. The encoder 658 may encode the serialized retrieved measurement information. The clamp/modulator 646 may modulate the current flowing through the inductive element 114 (e.g., coil 220) as a function of the encoded retrieved measurement information. In this way, the encoded retrieved measurement information may be conveyed by the inductive element 114 as a modulated electromagnetic wave. In some embodiments, the encoded retrieved measurement information conveyed by the sensor 100 may be received by the sensor reader 1500.

Figure 20:
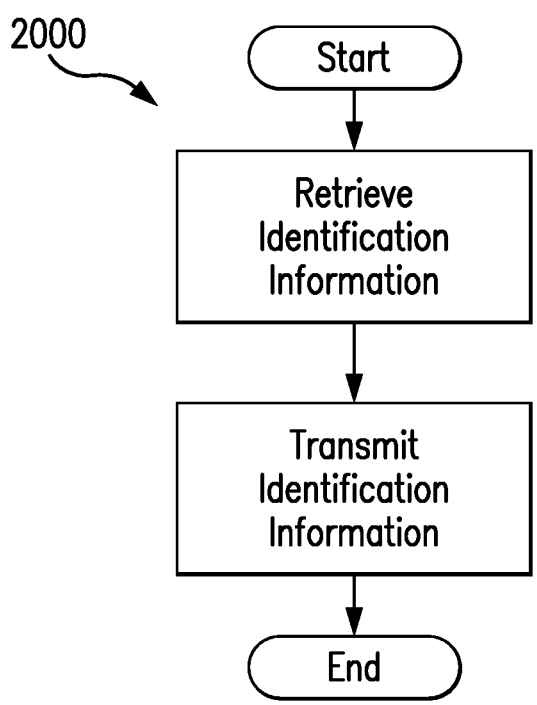
FIG. 20 illustrates a get identification information command execution process that may be performed by the sensor to execute a get identification information command received by the sensor in accordance with an embodiment of the present invention.

FIG. 20 illustrates a get identification information command execution process 2000 that may be performed in step 1610 of the sensor control process 1600 by the sensor 100 to execute a get identification information command received by the sensor 100 in accordance with an embodiment of the present invention. The get identification information command execution process 2000 may begin with a step 2002 of retrieving stored identification information. In some embodiments, identification information is stored in the nonvolatile storage medium 660. In response to a request from the measurement controller 532, the nonvolatile storage medium 660 may output identification information to the data and control bus 654. In some embodiments, the data and control bus 654 may transfer the retrieved identification information to the measurement controller 532. However, in alternative embodiments, the data and control bus 654 may transfer the retrieved identification information to the command decoder/data encoder 652 without first transferring the retrieved identification information to the measurement controller 532.

After the stored identification information is retrieved, the get identification information command execution process 2000 may proceed to a step 2004 in which the sensor 100 may convey the retrieved identification information. In one embodiment, the measurement controller 532 may output the retrieved identification information to the data and control bus 654. The data and control bus 654 may transfer the identification information to the command decoder/data encoder 652, which may encode the identification information. The data serializer 656 may serialize the encoded identification information. The encoder 658 may encode the serialized identification information. The clamp/modulator 646 may modulate the current flowing through the inductive element 114 (e.g., coil 220) as a function of the encoded retrieved identification information. In this way, the encoded identification information may be conveyed by the inductive element 114 as a modulated electromagnetic wave. In some embodiments, the encoded identification information conveyed by the sensor 100 may be received by the sensor reader 101.

The sensor 100 may be capable of executing other commands received by the sensor. For example, the sensor 100 may perform a setup parameter update execution process that may be performed in step 1610 of the sensor control process 1600 by the sensor 100 to execute a command to update setup parameters. In some embodiments, the setup parameter update execution process may replace one or more setup parameters (i.e., initialization information) stored in the nonvolatile storage medium 660. In one embodiment, upon receiving a command to update setup parameters, the measurement controller 532 may output one or more setup parameters received with the command to the data and control bus 654, which may transfer the setup parameter(s) to the nonvolatile storage medium 660. The nonvolatile storage medium 660 may store the received setup parameter(s). In a non-limiting embodiment, the received setup parameter(s) may replace one or more setup parameters previously stored in the nonvolatile storage medium 660.

Figure 22:
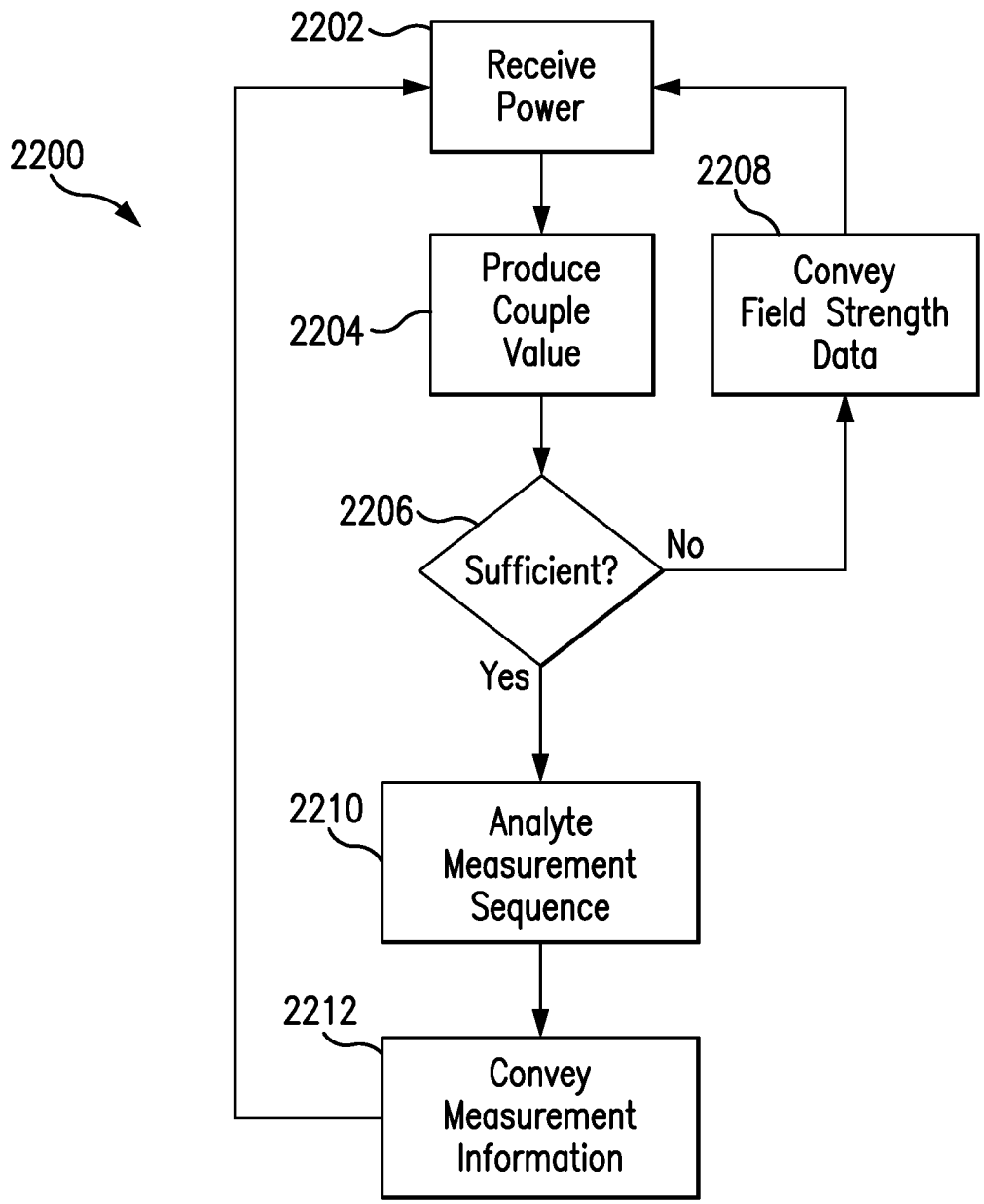
FIG. 22 illustrates an alternative sensor control process that may be performed by the sensor in accordance with an embodiment of the present invention.

FIG. 22 illustrates an alternative sensor control process 2200 that may be performed by the sensor 100, which may be, for example, implanted within a living animal (e.g., a living human), in accordance with an embodiment of the present invention. The sensor control process 2200 may begin with a step 2202 of coupling the inductive element of the external reader 101 and the inductive element 114 of the sensor 100 within an electrodynamic field. The sensor 100 may use the electrodynamic field to generate operational power. In one embodiment, the electrodynamic field may be received using the inductive element 114 of the sensor 100. The electrodynamic field may induce a current in inductive element 114, and the input/output (I/O) front end block 536 may convert the induced current into power for operating the sensor 100. In a non-limiting embodiment, rectifier 640 may be used to convert the induced current into operating power for the sensor 100.

In step 2204, circuitry of the sensor 100 may produce a coupling value proportional to the strength of the coupling of the inductive element of the external reader 101 and the inductive element 114 of the sensor 100. In some non-limiting embodiments, the clamp/modulator 646 of the I/O circuit 536 may produce a coupling value (e.g., $I_{couple}$) proportional to the received field strength based on the current induced in the inductive element 114 by the electrodynamic field. In one non-limiting embodiment, the coupling value proportional to the field strength may be converted (e.g., by ADC 664) to a digital coupling value proportional to the received field strength.

In step 2206, the reader may use the analog and/or digital coupling value to determine whether the strength of the electrodynamic field received by the sensor 100 is sufficient for the sensor 100 to perform an analyte measurement. For instance, in one non-limiting embodiment, the measurement controller 532 may compare the digital coupling value to an analyte measurement field strength sufficiency threshold and produce an indication that the strength of the electrodynamic field received by the sensor is either sufficient or insufficient for the implanted sensor to perform the analyte measurement.

If the sensor 100 determines that the strength of the electrodynamic field received by the sensor 100 is insufficient, in step 2208, the sensor 100 may convey the field strength data including the analog or digital coupling value and/or the indication that the strength of the electrodynamic field received by the sensor is either sufficient or insufficient to the external sensor reader 101 (e.g., by modulating the electrodynamic field based on the field strength data). In one embodiment, the measurement controller 532 may output the field strength data to the data and control bus 654. The data and control bus 654 may transfer the field strength data to the command decoder/data encoder 652, which may encode the field strength data. The data serializer 656 may serialize the encoded field strength data. The encoder 658 may encode the serialized field strength data. The clamp/modulator 646 may modulate the current flowing through the inductive element 114 (e.g., coil 220) as a function of the encoded field strength data. In this way, the encoded field strength data may be conveyed by the inductive element 114 as a modulated electromagnetic wave. In some embodiments, the encoded field strength data conveyed by the sensor 100 may be received by the sensor reader 101.

If the sensor 100 determines that the strength of the electrodynamic field received by the sensor 100 is sufficient, in step 2210, the sensor 100 may automatically execute an analyte measurement sequence (e.g., the analyte measurement command execution process 1700 shown in FIG. 17) and generate analyte measurement information.

In step 2212, the sensor 100 may the sensor 100 may convey the analyte measurement information to the sensor reader 101 using the inductive element 114. In one embodiment, the measurement controller 532 may output the analyte measurement information to the data and control bus 654. The data and control bus 654 may transfer the analyte measurement information to the command decoder/data encoder 652, which may encode the analyte measurement information. The data serializer 656 may serialize the encoded analyte measurement information. The encoder 658 may encode the serialized field strength data. The clamp/modulator 646 may modulate the current flowing through the inductive element 114 (e.g., coil 220) as a function of the encoded analyte measurement information. In this way, the encoded analyte measurement information may be conveyed by the inductive element 114 as a modulated electromagnetic wave. In some embodiments, the encoded analyte measurement information conveyed by the sensor 100 may be received by the sensor reader 101.

Figure 23:
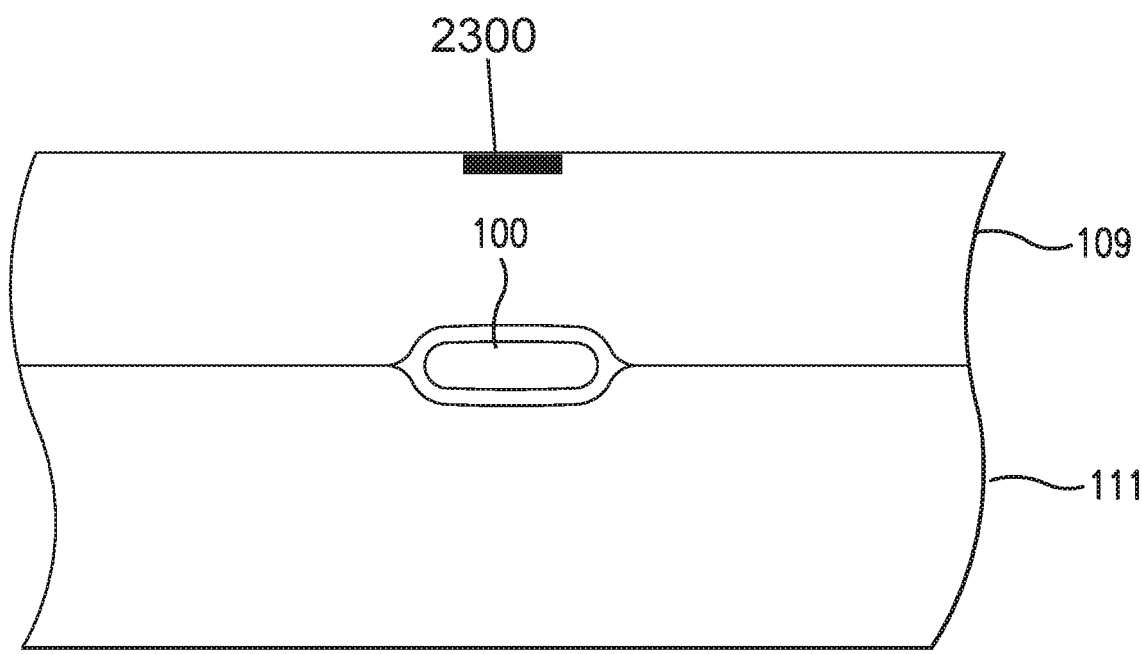
FIG. 23 is a reference mark on the skin for use in making a precise incision for removing the sensor, emobdying apsects of the present invention.

In another embodiment, the field strength system may be utilized as a convenient sensor locator to be used when physicians wish to remove the sensor 100 following its useful life in vivo. The sensor 100 is not visible when implanted in the subcutaneous space, and it is not always easy to palpate under the skin for some users that may have more adipose tissue in the space. As shown in FIG. 23, the field strength trigger system may be configured as a pinpoint locator function joined with a set marking on the reader case to provide physicians with the ability use the reader to place a reference mark 2300 on the skin 109 for use in making a precise incision for removing the sensor 100 without having to guess the exact location of the implant and where the incision is to be made for most efficient removal.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, while the invention has been described with reference to a case or reader coupled to a smartphone, the sensor reader can be an independent box or a key fob that communicates to a smartphone or computer through Bluetooth or a physical cable connection. In addition, circuitry of the sensor 100 and reader 101 may be implemented in hardware, software, or a combination of hardware or software. The software may be implemented as computer executable instructions that, when executed by a processor, cause the processor to perform one or more functions.

What is claimed is:

1. A method locating a sensor implanted within a living animal, the method comprising:
    generating, using an external reader, field strength data indicative of the strength of coupling of an inductive element of the external reader and an inductive element of the sensor within an electrodynamic field while the external reader is at each of a plurality of locations relative to the location of the sensor; and
    using the external reader to place a reference mark on skin of the living animal at the location of the plurality of locations at which field strength data indicative of the strongest strength of coupling was generated.

2. The method of locating of claim 1, wherein the external reader generates the field strength data by producing, using circuitry of the external sensor, a coupling value proportional to the strength of the coupling of the inductive element of the external reader and the inductive element of the sensor.

3. A method locating a sensor implanted within a living animal, the method comprising:
- generating, using an external reader, first field strength data indicative of the strength of coupling of an inductive element of the external reader and an inductive element of the sensor within an electrodynamic field while the external reader is at a first location relative to the location of the sensor;
- generating, using the external reader, second field strength data indicative of the strength of coupling of the inductive element of the external reader and an inductive element of the sensor within an electrodynamic field while the external reader is at a second location relative to the location of the sensor;
- comparing the first field strength data and the second field strength data;
- if the first field strength data indicates a stronger strength of coupling than the strength of coupling indicated by the second field strength data, determining that the location of the sensor is closer to the first location than the second location; and
- if the second field strength data indicates a stronger strength of coupling than the strength of coupling indicated by the first field strength data, determining that the location of the sensor is closer to the second location than the first location.

4. The method of locating of claim 3, further comprising using the external reader to place a reference mark on skin of the living animal at the location of the first and second locations determined to be closer to the location of the sensor.

5. The method of locating of claim 3, wherein the external reader generates the first and second field strength data by producing, using circuitry of the external sensor, first and second coupling values proportional to the strength of the coupling of the inductive element of the external reader and the inductive element of the sensor while the external reader is at the first and second locations relative to the location of the sensor, respectively.

6. An external reader for locating a sensor implanted within a living animal, the external reader comprising:
- (a) an inductive element configured to couple with an inductive element of an external reader within electrodynamic field;
- (b) circuitry configured to generate field strength data indicative of the strength of coupling of an inductive element of the external reader and an inductive element of the sensor within an electrodynamic field while the external reader is at each of a plurality of locations relative to the location of the sensor; and
- (c) a marking element configured to place a reference mark on skin of the living animal at the location of the plurality of locations at which field strength data indicative of the strongest strength of coupling was generated.

* * * * *